(12) United States Patent
Palasis et al.

(10) Patent No.: US 6,800,073 B2
(45) Date of Patent: *Oct. 5, 2004

(54) BIOCOMPATIBLE PHARMACEUTICAL ARTICLES

(75) Inventors: Maria Palasis, Wellsley, MA (US); Wendy Naimark, Cambridge, MA (US); Timothy Mickley, Elk River, MN (US); Justin Crank, Minneapolis, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/845,092

(22) Filed: Apr. 27, 2001

(65) Prior Publication Data

US 2002/0055721 A1 May 9, 2002

Related U.S. Application Data

(63) Continuation-in-part of application No. 09/429,178, filed on Oct. 28, 1999, now Pat. No. 6,638,259, and a continuation-in-part of application No. 09/503,586, filed on Feb. 14, 2000, now Pat. No. 6,663,606.

(51) Int. Cl.[7] .......................... A61M 25/00; A61M 5/32
(52) U.S. Cl. ........................................ 604/264; 604/272
(58) Field of Search ..................... 604/890.1, 891.1, 604/892.1, 130, 264–266, 272; 623/1.44, 1.46, 1.45; 427/2.12, 2.25

(56) References Cited

U.S. PATENT DOCUMENTS

| | | | | |
|---|---|---|---|---|
| 2,814,296 A | * | 11/1957 | Everett et al. | ............... 604/264 |
| 4,838,877 A | | 6/1989 | Massau | ....................... 604/272 |
| 5,098,977 A | | 3/1992 | Frautschi et al. | ........... 527/313 |
| 5,266,359 A | | 11/1993 | Spielvogel | ................ 427/388.4 |
| 5,368,048 A | | 11/1994 | Stoy et al. | ................... 128/772 |
| 5,607,401 A | | 3/1997 | Humphrey | ................... 604/239 |
| 5,637,399 A | | 6/1997 | Yoshikawa et al. | ......... 428/369 |
| 5,671,754 A | | 9/1997 | Schmukler et al. | ......... 128/844 |
| 6,059,738 A | | 5/2000 | Stoltze et al. | ............... 600/585 |
| 6,120,536 A | | 9/2000 | Ding et al. | ................. 623/1.43 |

FOREIGN PATENT DOCUMENTS

| EP | 0 798 398 A2 | 10/1997 | ............. C23C/8/38 |
|---|---|---|---|
| WO | WO 92/05829 | 4/1992 | .......... A61M/29/00 |
| WO | WO 94/16836 | 8/1994 | ............. B08B/3/12 |
| WO | WO 98/40469 | 9/1998 | ............. C12N/5/12 |
| WO | WO 98/53762 | 12/1998 | ............. A61F/2/06 |
| WO | WO 99/22655 | 5/1999 | ........... A61B/17/32 |
| WO | WO 99/62395 | 12/1999 | |
| WO | WO 00/76573 A1 | 12/2000 | .......... A61M/31/00 |

OTHER PUBLICATIONS

"Standard Specification for Chemical Passivation for Stainless Steel Parts," American Society for Testing and Materials, Designation A 967–96, pp. 1–6.

Marshall, Deborah J., et al. "Biocompatibility of Cardiovascular Gene Delivery Catheters with Adenovirus Vectors: An Important Determinant of the Efficiency of Cardiovascular Gene Transfer," Molecular Therapy, vol. 1, No. 5, May 2000, Part 1 of 2 Parts, p. 423–429.

* cited by examiner

Primary Examiner—Sharon Kennedy
(74) Attorney, Agent, or Firm—Mayer Fortkort & Williams, PC; David B. Bonham, Esq.

(57) ABSTRACT

Many conventional pharmaceutical articles contain seemingly inert components that come into contact with a pharmaceutically active material during use, which contact substantially reduces the pharmaceutical effectiveness of the pharmaceutically active material. The invention described herein concerns various modifications to these incompatible components, which are effective to diminish the reduction in pharmaceutical effectiveness.

19 Claims, 12 Drawing Sheets

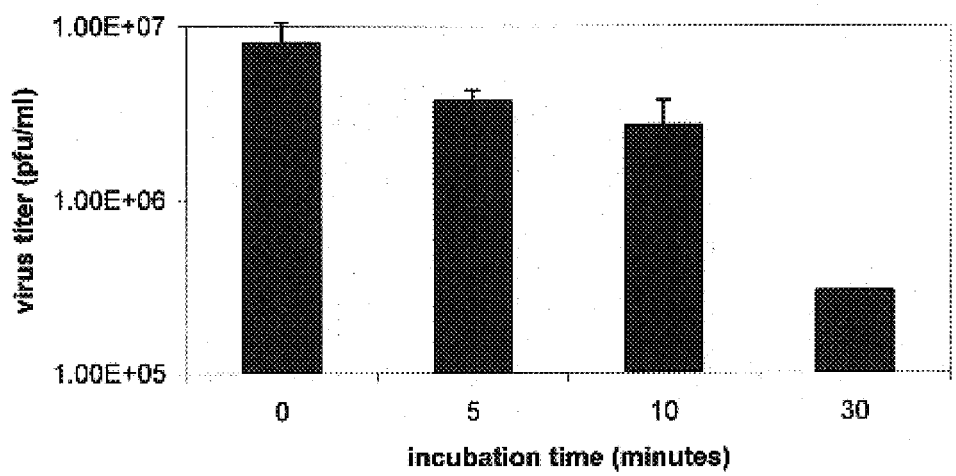
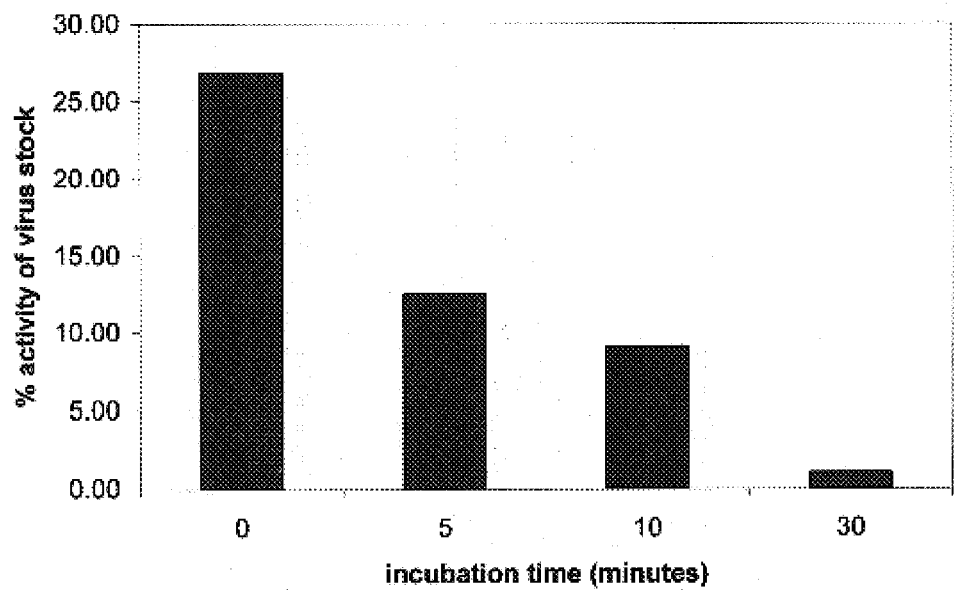

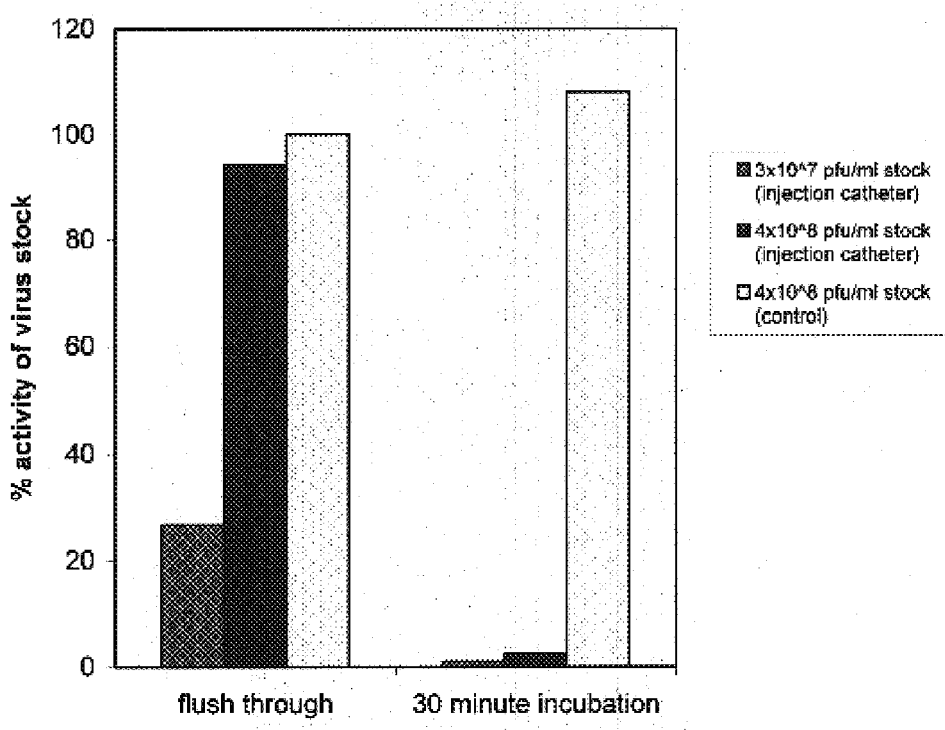
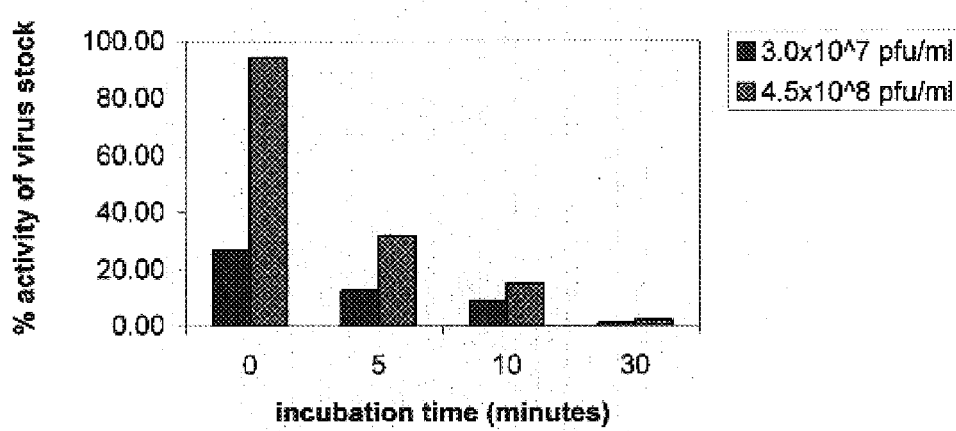

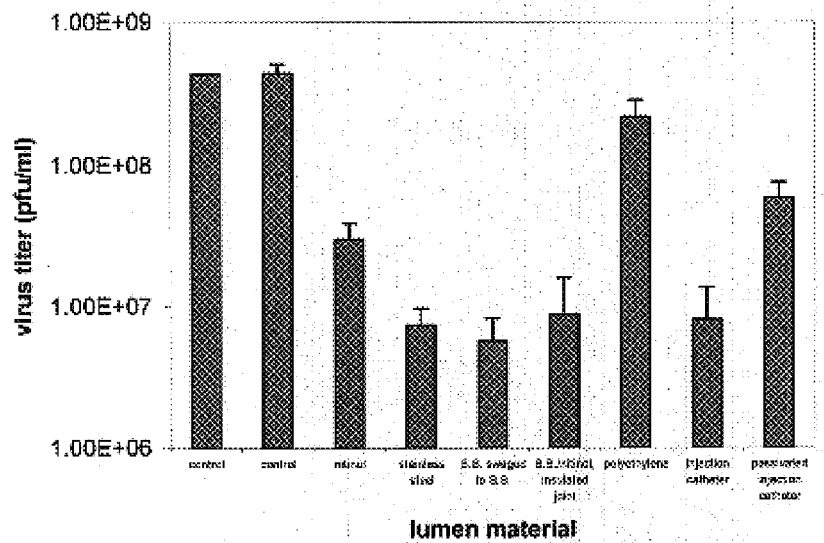
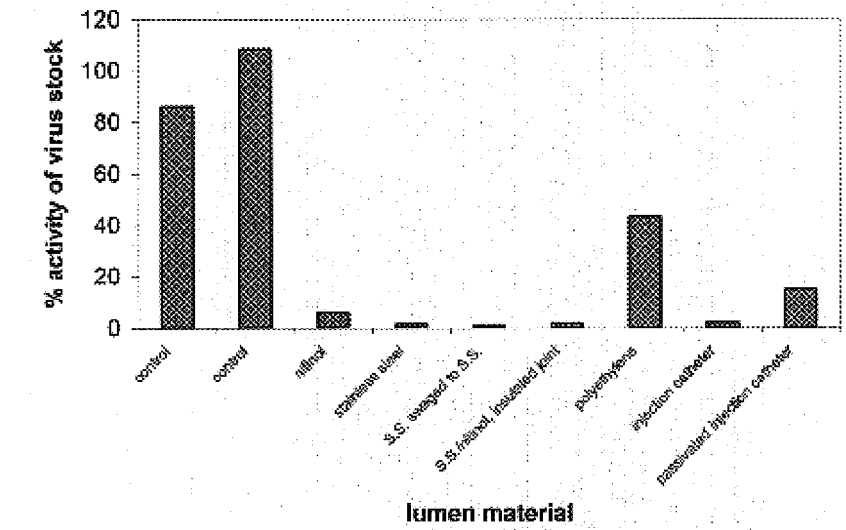

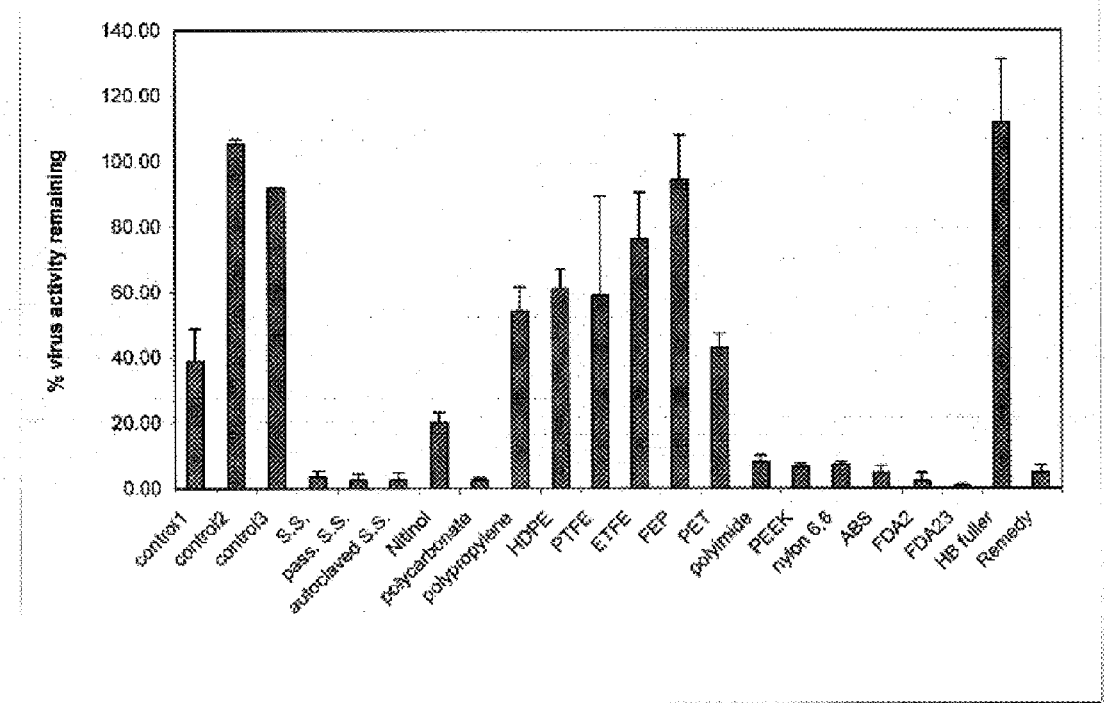

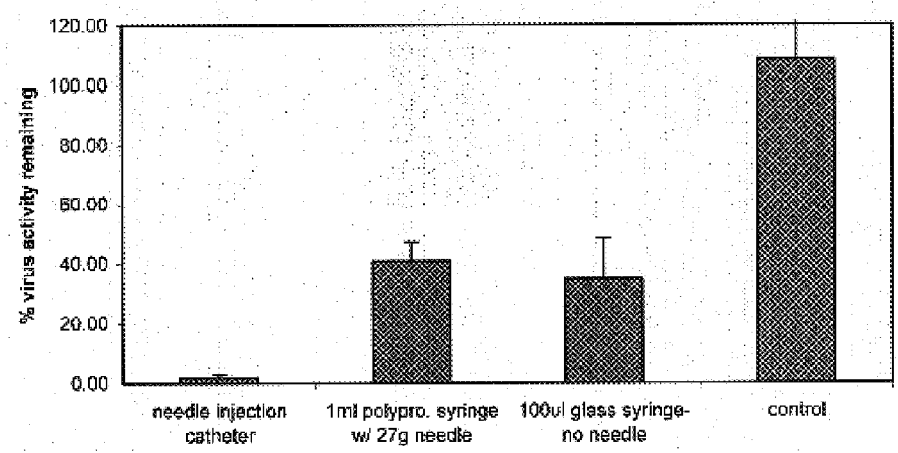
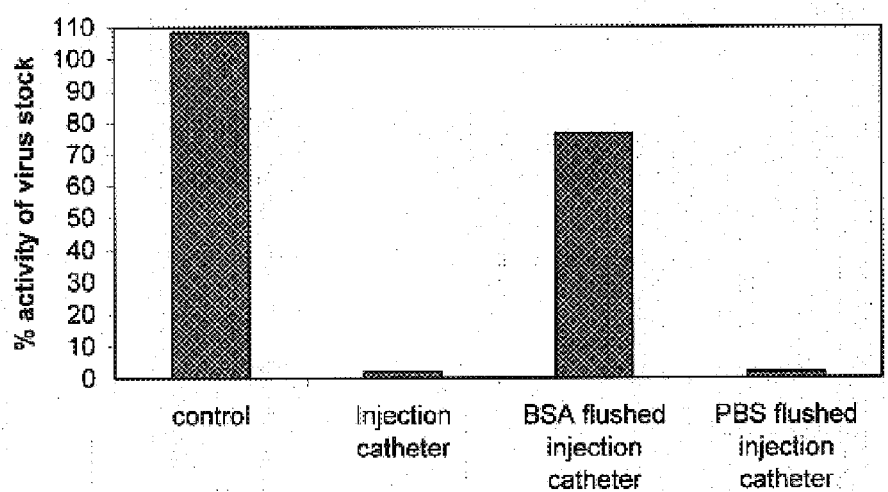

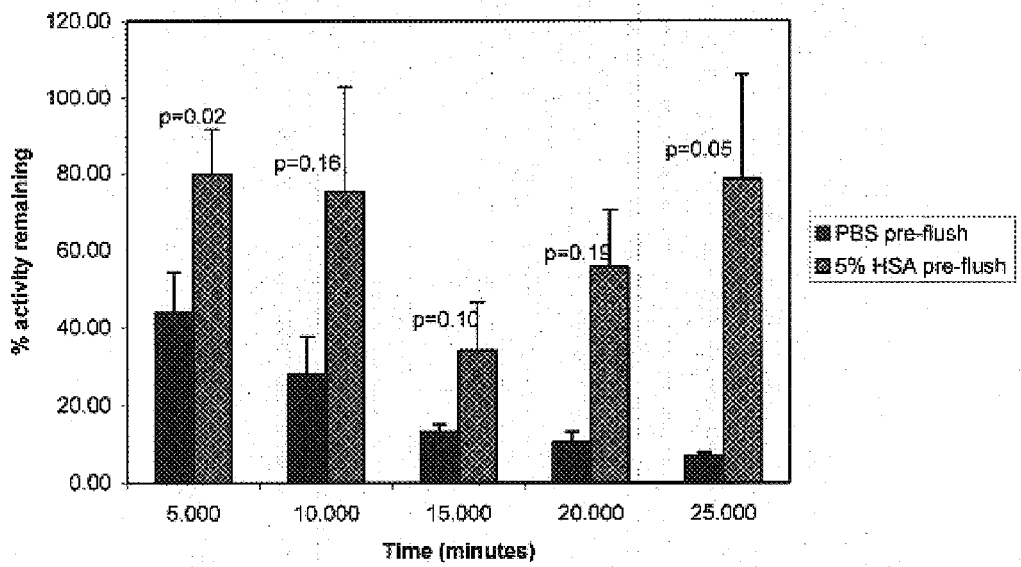
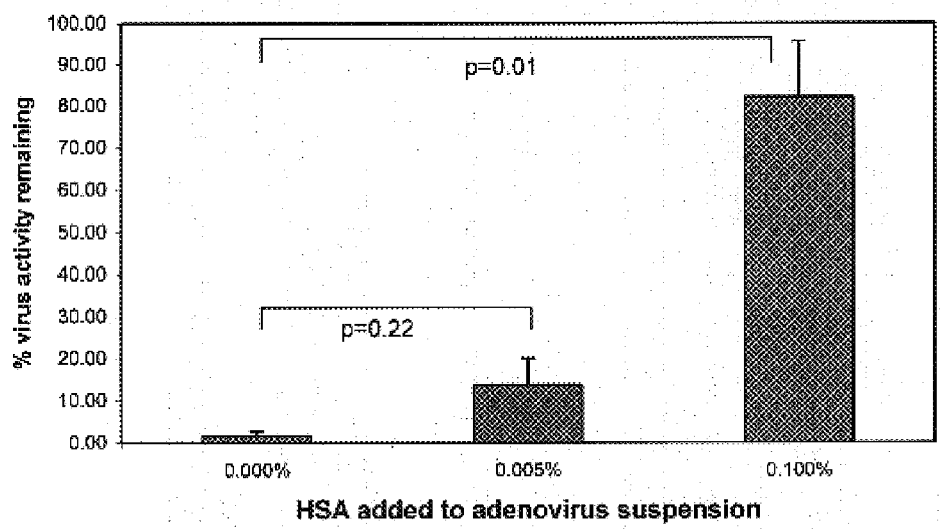

Virus Concentration post Treatment

Virus Concentration post Treatment

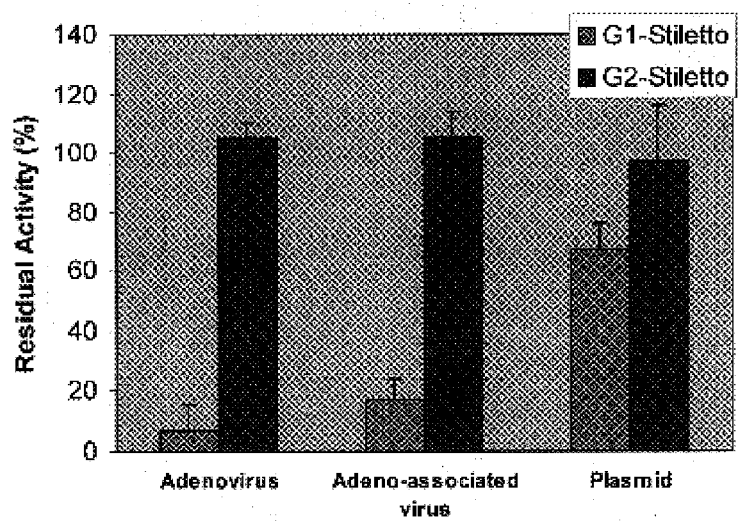
Fig. 14a. Vector Effects
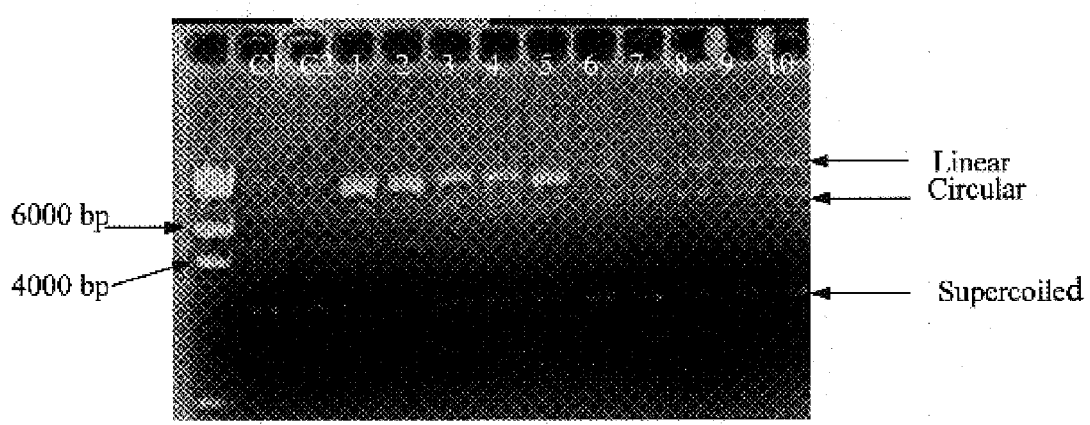
Fig. 14b. Assessment of plasmid DNA structural integrity

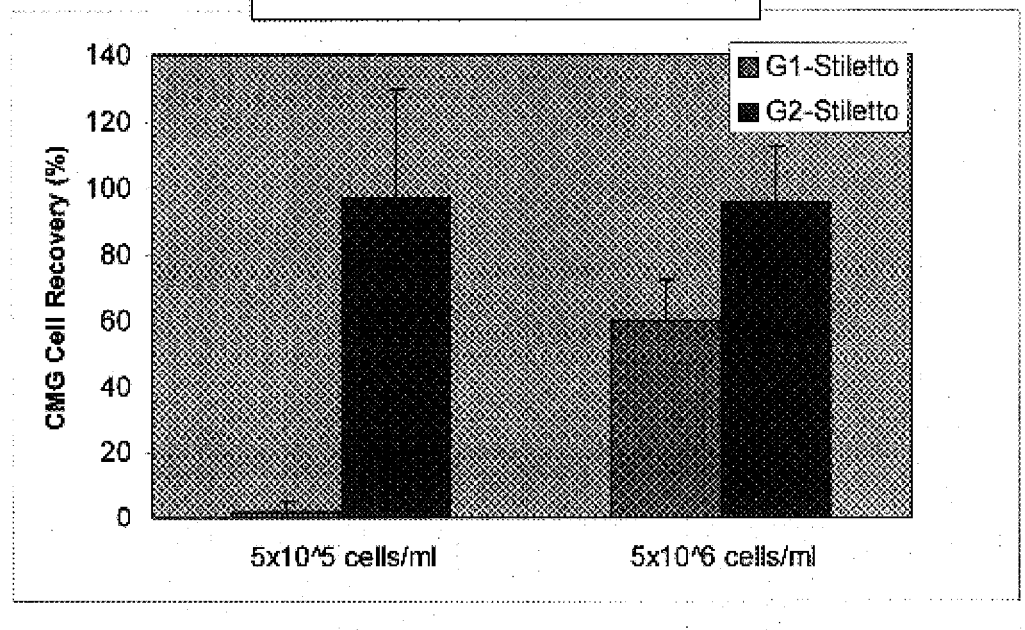

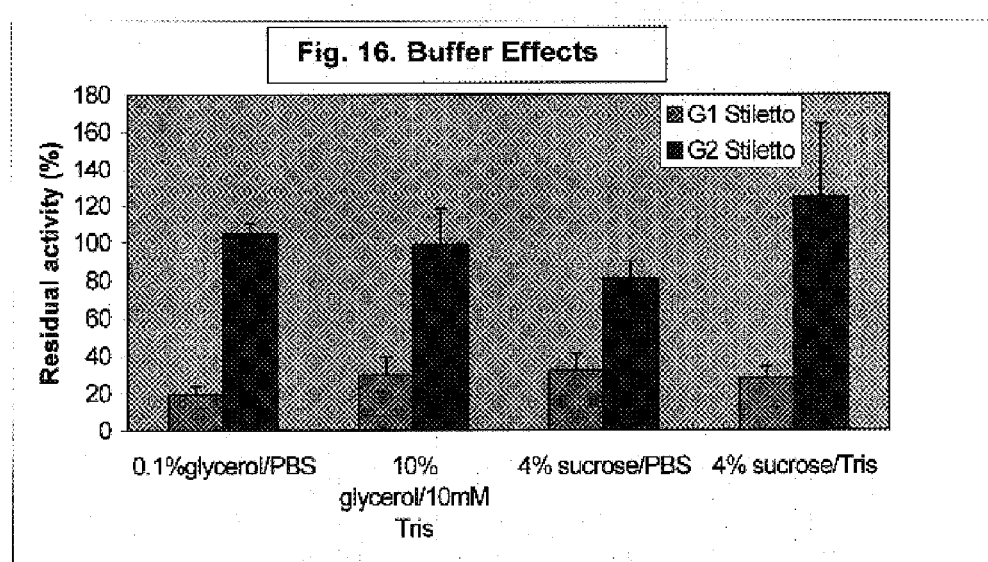
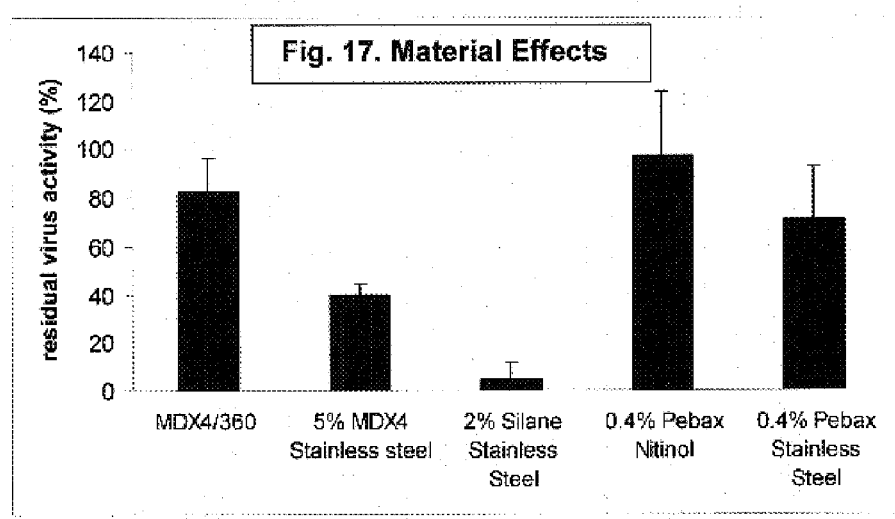

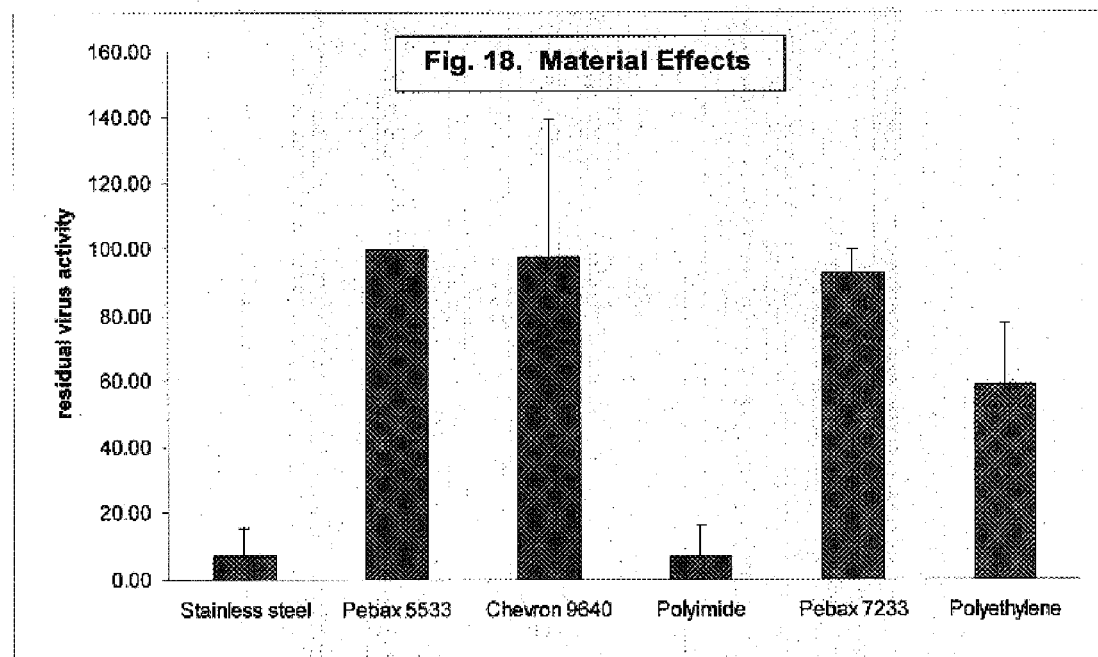
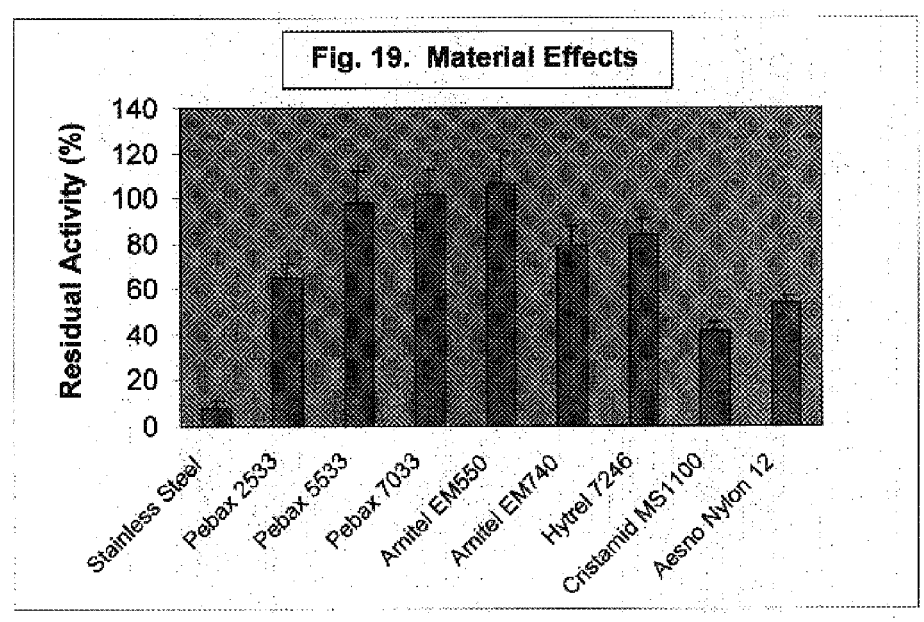

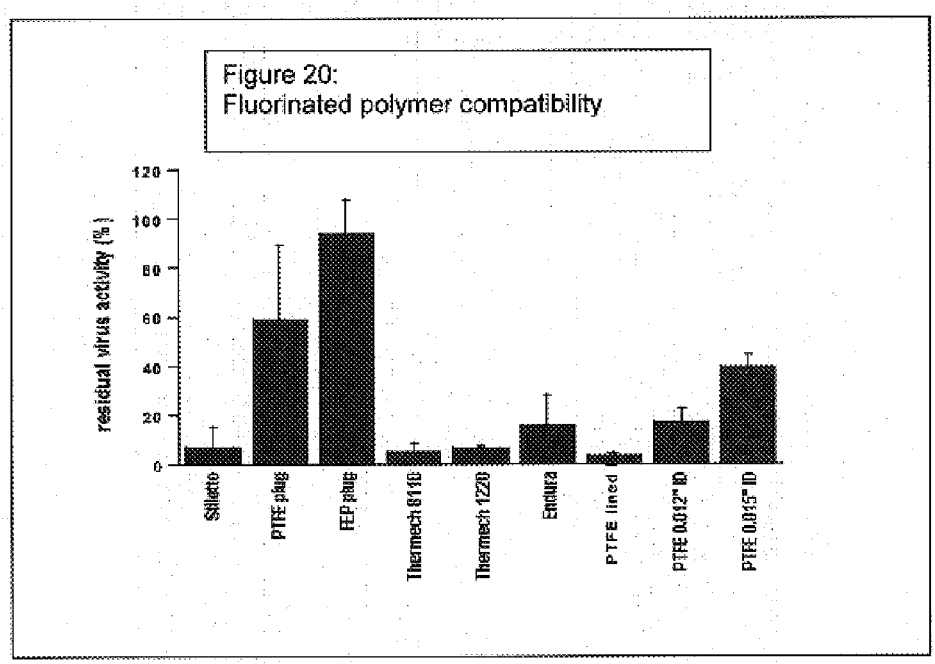

BIOCOMPATIBLE PHARMACEUTICAL ARTICLES

STATEMENT OF RELATED APPLICATIONS

This is a continuation-in-part of U.S. Ser. No. 09/429,178 filed Oct. 28, 1999 and entitled "Biocompatible Medical Devices", now U.S. Pat. No. 6,638,259. This is also a continuation-in-part of U.S. Ser. No. 09/503,586 filed Feb. 14, 2000 and entitled "Biocompatible Medical Devices", now U.S. Pat. No. 6,663,606. Each of these applications is hereby incorporated by reference in its entirety.

FIELD OF THE INVENTION

The present application relates to pharmaceutical articles that come into contact with pharmaceutically active materials and are compatible with the same.

BACKGROUND OF THE INVENTION

Pharmaceutically active materials typically come into contact with other materials at various points in the product life cycle, including manufacture, analysis, storage and delivery. Frequently, these other materials are constructed of a material component that is believed to be compatible with the pharmaceutically active material.

For instance, it is known to contact pharmaceutically active materials with various pharmaceutical articles, including medical devices as well as manufacturing, storage and transport equipment, which have metallic and/or polymeric components. Metallic components selected for this purpose are numerous and include certain titanium alloys (e.g., nickel-titanium super-elastic alloys such as nitinol) and stainless steel. These materials are commonly used for this purpose as they are formable, have desirable mechanical properties and are commonly believed to be substantially inert. Also used are numerous polymeric components that are commonly believed to be substantially inert, including certain polycarbonate, polyimide, acrylonitrile/butadiene/styrene resin, poly ether ether ketone, epoxy, and nylon materials.

The present inventors have found, however, that such materials can be relatively incompatible with certain pharmaceutically active materials. As a result, there is at present a need in the art to overcome these incompatibilities and others like them.

BRIEF DESCRIPTION OF THE FIGURES

FIG. 1 presents absolute virus titer (log scale) as a function of time for an untreated injection catheter.

FIG. 2 presents the data of FIG. 1 as a percentage of viral stock titer (linear scale).

FIG. 3 presents virus titer (as a percentage of virus stock titer): (a) after 0 (flush through) and 30 minutes for a control (4E+08 pfu/ml initial titer), (b) after 0 (flush through) and 30 minutes for an injection catheter constructed of stainless steel and nitinol, using the same stock virus titer as the control (4E+08 pfu/ml initial titer), and (c) after 0 (flush through) and 30 minutes for an injection catheter constructed of stainless steel and nitinol, using a lower stock virus titer (3E+07 pfu/ml initial titer).

FIG. 4 presents virus titer (as a percentage of virus stock titer) after 0 (flush through), 5, 10 and 30 minutes an injection catheter constructed of stainless steel and nitinol for two viral solutions (3.0E+7 pfu/ml and 4.5E+8 pfu/ml initial titer).

FIG. 5 presents absolute virus titer (log scale) after 30 minute incubation in the following materials: a nitinol lumen, a stainless steel lumen, a lumen of stainless steel swaged to nitinol, a lumen of stainless steel swaged to nitinol with an insulated joint, a polyethylene lumen, an injection catheter constructed of stainless steel and nitinol, and a passivated injection catheter constructed of stainless steel and nitinol.

FIG. 6 presents the data of FIG. 5 as a percentage of viral stock titer (linear scale).

FIG. 7 presents virus titer as a percentage of viral stock titer (linear scale) after 30 minute incubation in connection with the following materials: stainless steel, passivated stainless steel, autoclaved stainless steel, nitinol, polycarbonate, polypropylene, high density polyethylene (HDPE), polytetrafluoroethylene (PTFE), modified ethylene-tetrafluoroethylene copolymer (ETFE), poly (tetrafluoroethylene-co-hexafluoropropene)(FEP), polyethylene terephthalate polyester (PET-P), polyimide, poly ether ether ketone (PEEK), nylon 6/12, acrylonitrile/butadiene/styrene resin (ABS), FDA2, FDA23, HP Fuller, and a REMEDY infusion balloon catheter.

FIG. 8 presents virus titer as a percentage of viral stock titer (linear scale) after 30-minute incubation within a needle injection catheter, a polypropylene syringe (with needle), a glass syringe (without needle) and a control.

FIG. 9 presents virus titer as a percentage of viral stock titer (linear scale) after 30-minute incubation within a control vial, an untreated needle injection catheter, a needle injection treated flushed with BSA and a needle injection catheter treated with PBS. The BSA- and PBS-treated catheters were provided by flushing with BSA and PBS solutions prior to incubation with virus.

FIG. 10 presents virus titer as a percentage of viral stock titer (linear scale) for needle injection catheters pre-flushed with 5% HSA solution and PBS solution. Viral solution is pushed through the catheters and analyzed at 5, 10, 15, 20 and 25 minutes.

FIG. 11 presents virus titer as a percentage of viral stock titer (linear scale) for adenoviral solutions containing HSA concentrations of 0% (no HSA addition), 0.005% and 0.1%, after incubation within a need injection catheter for 30 minutes.

FIG. 14a presents activity for various gene vectors after incubation in both an unlined needle injection catheter and an injection catheter lined with polyether block amide.

FIG. 14b presents a structural assessment of plasmid DNA following incubation in both an unlined needle injection catheter and an injection catheter lined with polyether block amide.

FIG. 15 presents the number of viable cells recovered (normalized to a control) obtained after incubation in both an unlined needle injection catheter and an injection catheter that is lined with polyether block amide. Two cell concentrations ($5 \times 10^5$ cells/ml and $5 \times 10^6$ cells/ml) are presented.

FIG. 16 presents virus titer as a percentage of viral stock titer (linear scale) for four adenoviral solutions with differing buffer systems, after incubation in an unlined needle injection catheter and an injection catheter lined with polyether block amide.

FIG. 17 presents virus titer as a percentage of viral stock titer (linear scale) for adenoviral solution after incubation in various lumens.

FIG. 18 presents virus titer as a percentage of viral stock titer (linear scale) for adenoviral solution after incubation in catheters fabricated with various extruded shaft materials.

FIG. 19 presents virus titer as a percentage of viral stock titer (linear scale) for adenoviral solution after incubation in contact with various extruded shaft materials.

FIG. 20 presents virus titer as a percentage of viral stock titer (linear scale) for adenoviral solution after being incubated with various fluorocarbon materials, either as plugs, coatings or liners.

SUMMARY OF THE INVENTION

Figure 12:
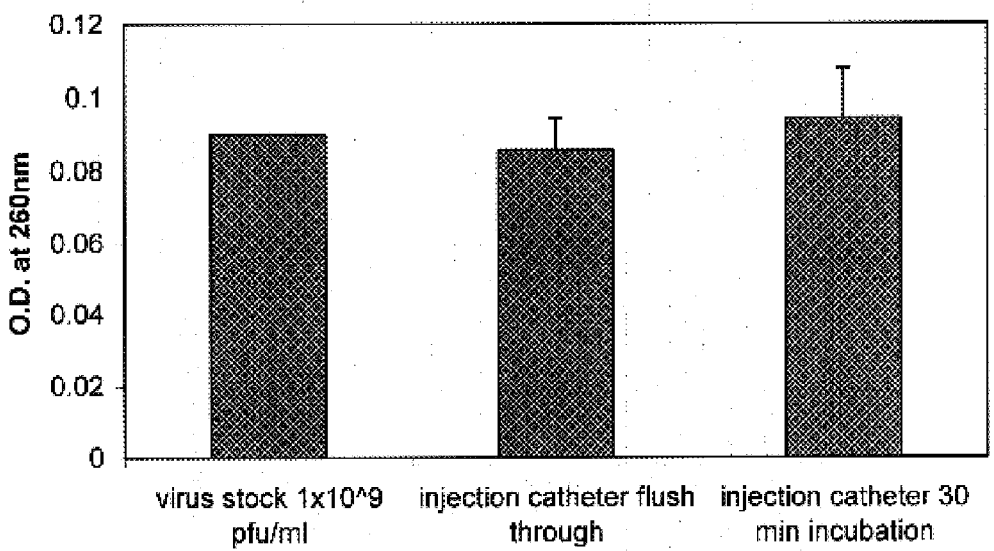
FIG. 12 presents OD 260 data for (a) virus stock, (b) virus stock after flushing through an injection catheter constructed of stainless steel and nitinol, and (c) virus stock after 30-minute incubation in an injection catheter constructed of stainless steel and nitinol.

According to an embodiment of the invention, a modified pharmaceutical article is provided. The pharmaceutical article comprises an incompatible material that acts to substantially reduce the pharmaceutical effectiveness of a pharmaceutically active material upon contact. To address this issue, this incompatible material is either replaced, or a barrier layer is disposed between the incompatible material and the pharmaceutically active material.

According to another embodiment of the invention, a pharmaceutical article for contact with a pharmaceutically active material is provided. The pharmaceutical article comprises: (a) a lumen comprising an incompatible material that acts to substantially reduce the pharmaceutical effectiveness of the pharmaceutically active material upon contact; and (b) a barrier layer disposed between the incompatible material and the pharmaceutically active material, wherein the barrier layer is more compatible with the pharmaceutically active material than is the incompatible material.

In some instances, the incompatible material comprises certain metals, such as stainless steel and nickel-titanium alloys. In other instances, the incompatible material comprises certain polymers, such as polycarbonate, polyimide, poly ether ether ketone (PEEK), nylon and acrylonitrile/butadiene/styrene resin.

The barrier layer can comprise, for example, an inorganic material, such as carbon, fused silica fibers, or metal (e.g., titanium, gold and/or platinum). The barrier layer can also comprise a polymeric material, which can be, for example, in the form of a polymer coating or a preformed polymer layer. Preferred polymers include polyalkylene polymers and copolymers, fluorocarbon polymers and copolymers, polyester polymers and copolymers, polyether polymers and copolymers, silicone polymers and copolymers, and polyurethane polymers and copolymers. More preferred polymers are selected from polyethylenes, polypropylenes, polytetrafluoroethylenes, poly(tetrafluoroethylene-co-hexafluoropropenes), modified ethylene-tetrafluoroethylene copolymers, ethylene chlorotrifluoroethylene copolymers, polyvinylidene fluorides, polyethylene oxides, polyethylene terephthalates, silicones, polyurethanes, polyether block amides and polyether esters.

Preferred pharmaceutically active materials for use in connection with the present invention include those comprising polynucleotides, for example, viral vectors, plasmids and whole cells.

According another embodiment of the present invention, a needle injection catheter for delivery of a pharmaceutically active material into bodily tissue is provided. The needle injection catheter comprises: (a) a conventional needle injection catheter that includes an incompatible material which acts to substantially reduce the pharmaceutical effectiveness of the pharmaceutically active material upon contact with the incompatible material; and (b) a barrier layer (which is more compatible with the pharmaceutically active material than is the incompatible material) disposed between the incompatible material and the pharmaceutically active material.

According to another embodiment of the present invention, a needle injection catheter for delivery of a pharmaceutically active material into bodily tissue is provided by a method comprising: (a) providing a conventional needle injection catheter, which comprises an incompatible material that comes into contact with a pharmaceutically active material and acts to substantially reduce pharmaceutical effectiveness of the pharmaceutically active material upon contact; and (b) replacing at least a portion of the incompatible material with a more compatible material, such that the substantial reduction in the pharmaceutical effectiveness of the pharmaceutically active material is diminished.

Preferably, the needle injection catheter comprises: (a) a body portion, which further comprises a lumen, and (b) a needle portion in fluid communication with the body portion.

According to another embodiment of the invention, a drug delivery catheter for endoluminal delivery of a pharmaceutically active material into bodily tissue (e.g., a perfusion catheter) is provided. The catheter comprises: (a) a conventional endoluminal delivery catheter that comprises an incompatible material which acts to substantially reduce the pharmaceutical effectiveness of the pharmaceutically active material upon contact; and (b) a barrier layer, which is more compatible with the pharmaceutically active material than is the incompatible material, disposed between the incompatible material and the pharmaceutically active material.

According to another embodiment of the invention, a drug delivery catheter for endoluminal delivery of a pharmaceutically active material into bodily tissue is provided by a method comprising: (a) providing a conventional endoluminal delivery catheter that includes an incompatible material which comes into contact with a pharmaceutically active material and acts to substantially reduce pharmaceutical effectiveness of the pharmaceutically active material upon contact; and (b) replacing at least a portion of the incompatible material with a more compatible material, such that the substantial reduction in the pharmaceutical effectiveness of the pharmaceutically active material is diminished.

One advantage of the present invention is that incompatibility problems, which are presently experienced when components of medical articles come into contact with pharmaceutically active materials, are minimized.

Another advantage is that the pharmaceutical effectiveness of pharmaceutically active materials that come into contact with medical articles need not be substantially decreased.

Still other embodiments and advantages will become readily apparent to those of ordinary skill in the art upon review of the Detailed Description, Examples and claims set forth below.

DETAILED DESCRIPTION

As a preliminary matter, it is noted that "pharmaceutical article", as defined herein, means any article that comes into contact with a pharmaceutically active material.

By "pharmaceutical effectiveness" or "pharmaceutical efficacy" is meant any desired pharmaceutical result. As a specific example, the pharmaceutical effectiveness of a virus can be measured by the ability of that virus to infect cells. As another example, the pharmaceutical effectiveness of a protein can be measured by its activity within an ELISA assay.

Pharmaceutical effectiveness is said to be "substantially reduced" or is said to undergo a "substantial reduction" when it is reduced, for example, by at least 5%, more commonly 10%, 20%, 30%, 40%, 50% or more. An "incompatible component" is a component that causes a substantial reduction in pharmaceutical effectiveness upon contacting a pharmaceutically active material.

Likewise, pharmaceutical effectiveness is said to be "substantially increased" or is said to undergo a "substantial increase" when it is increased, for example, by at least 5%, more commonly 10%, 20%, 30%, 40%, 50% or more.

A first material is said to be "more compatible" with a given pharmaceutically active agent than is a second material, when contact with the first material results in a substantial increase in pharmaceutical effectiveness relative to contact with the second material. Likewise, a first material is said to be "less compatible" than a second material, when contact with the first material results in a substantial decrease in pharmaceutical effectiveness relative to contact with the second material.

Many pharmaceutical articles are known which come into contact with pharmaceutically active materials. However, as seen from the examples below, the present inventors have found that where certain materials commonly used in the manufacture of pharmaceutical articles come into contact with certain pharmaceutically active materials, pharmaceutical effectiveness is reduced substantially relative to contact with other substrates. Specifically, the present inventors have found that where certain pharmaceutically active materials, including certain viral gene vectors (such as adenovirus and adeno-associated virus), non-viral gene vectors (such as plasmids) and cells (such as cardiomyogenic cells) contact certain metallic materials (including certain stainless steel and/or nickel-titanium super alloys) or certain polymeric materials (including certain PEEK, polyimide, epoxy, nylon, ABS and/or polycarbonate polymers), pharmaceutical activity is substantially reduced relative to the same pharmaceutically active materials upon contact with other materials. This reduction is apparently due to inactivation and/or adsorption of the pharmaceutically active materials, for example, through denaturation, precipitation, damage, or other mechanism. This is surprising, since it is normally assumed that such materials are relatively inert and hence unlikely to interact with a pharmaceutically active material in an adverse fashion.

The present invention overcomes the above and other difficulties by providing pharmaceutical articles and methods in which one or more incompatible components that come into contact with pharmaceutically active materials are modified or replaced with a more compatible component. In this way, the articles and methods of the present invention prevent a substantial reduction in the pharmaceutical effectiveness of the pharmaceutically active materials.

The present invention is applicable to numerous conventional pharmaceutical articles (i.e., pharmaceutical articles in the prior art), including articles associated with the manufacture, storage, analysis and delivery of pharmaceutically active materials.

Specific pharmaceutical articles that are appropriate for the practice of the present invention include the following: (1) manufacturing articles, including fermentors, glassware, plasticware, probes and tubing; (2) storage and transport articles, including storage vessels, transport vessels, stoppers, lids and septums; (3) analytical articles including needles, pipette tips, cell culture apparatus and analytical equipment; (4) medical devices, including conventional needle syringes, hypodermic needles, intravenous injection devices, biopsy needles and devices, tissue ablation devices, aspirating needles, catheters, including endoluminal catheters such as needle injection catheters (for endocardial, epicardial, and pericardial agent administration), balloon catheters and diagnostic catheters and perfusion catheters, filters, grafts, metallic and polymeric stents, including those having a polymer coated thereon for delivery of pharmaceutically active materials, aneurysm filling coils, transmyocardial revascularization devices, percutaneous myocardial revascularization devices, soft tissue clips, sutures, blood clot filters, implants or spikes (polymeric or metallic); and (5) medical device accessories, including adhesives, coatings, balloons, membranes, manifolds, hubs, fittings, stopcocks, valves, tubing kits, manifolds, wires, syringes, microspheres or nanoparticles, and so forth.

Devices for drug delivery to the heart are of substantial interest and include, for example, those found in the following patents and patent applications: U.S. Pat. No. 5,450,846, U.S. Pat. No. 5,840,059, U.S. Pat. No. 5,878,751, U.S. Pat. No. 5,551,427, U.S. Pat. No. 5,931,834, U.S. Pat. No. 5,925,012, U.S. Pat. No. 5,925,033, U.S. Pat. No. 5,538,504, WO 99/39624, WO 99/44656, WO 99/21510, WO 99/29251, EP A 99-06 0895752, and EP A 99-01 0888750, each of which is incorporated herein by reference.

The medical devices contemplated for use in connection with the present invention include drug delivery medical devices that are used for either systemic treatment or for the treatment of any mammalian tissue or organ. Non-limiting examples are tumors; organs including but not limited to the heart, lung, brain, liver, kidney, bladder, urethra and ureters, eye, intestines, stomach, pancreas, ovary, and prostate; skeletal muscle; smooth muscle; breast; cartilage; and bone.

"Pharmaceutically active agents", "pharmaceutically active materials", "therapeutic agents", "drugs" and other related terms are used interchangeably herein and include genetic therapeutic agents, non-genetic therapeutic agents and cells. Pharmaceutically active agents useful in accordance with the present invention may be used singly or in combination.

Therapeutic agents include cells of human origin (autologous or allogeneic), including stem cells, or from an animal source (xenogeneic), which can be genetically engineered if desired to deliver proteins of interest. Cell types include bone marrow stromal cells, endothelial progenitor cells, myogenic cells including cardiomyogenic cells such as procardiomyocytes, cardiomyocytes, myoblasts such as skeletomyoblasts, fibroblasts, stem cells (e.g., mesenchymal, hematopoietic, neuronal and so forth), pluripotent stem cells, macrophage, satellite cells and so forth. Cells appropriate for the practice of the present invention also include biopsy samples for direct use (e.g., whole bone marrow) or fractions thereof (e.g., bone marrow stroma, bone marrow fractionation for separation of leukocytes). Where appropriate, media can be formulated as needed to maintain cell function and viability.

Therapeutic agents also include both polymeric (e.g., proteins, enzymes) and non-polymeric (e.g., small molecule therapeutics) agents and include Ca-channel blockers, serotonin pathway modulators, cyclic nucleotide pathway agents, catecholamine modulators, endothelin receptor antagonists, nitric oxide donors/releasing molecules, anesthetic agents, ACE inhibitors, ATII-receptor antagonists, platelet adhesion inhibitors, platelet aggregation inhibitors, coagulation pathway modulators, cyclooxygenase pathway inhibitors, natural and synthetic corticosteroids, lipoxygenase pathway inhibitors, leukotriene receptor antagonists, antagonists of E- and P-selectins, inhibitors of VCAM-1 and ICAM-1 interactions, prostaglandins and analogs thereof, macrophage activation preventers, HMG-CoA reductase inhibitors, fish oils and omega-3-fatty acids, free-radical scavengers/antioxidants, agents affecting various growth factors (including FGF pathway agents, PDGF receptor antagonists, IGF pathway agents, TGF-β pathway agents, EGF pathway agents, TNF-α pathway agents, Thromboxane A2 [TXA2] pathway modulators, and protein tyrosine kinase inhibitors), MMP pathway inhibitors, cell motility inhibitors, anti-inflammatory agents, antiproliferative/antineoplastic agents, matrix deposition/organization pathway inhibitors, endothelialization facilitators, blood rheology modulators, as well as integrins, chemokines, cytokines and growth factors.

Therapeutic agents also include genetic therapeutic agents and proteins, such as ribozymes, anti-sense polynucleotides and polynucleotides coding for a specific product (including recombinant nucleic acids) such as genomic DNA, cDNA, or RNA. The polynucleotide can be provided in "naked" form or in connection with vector systems that enhances uptake and expression of polynucleotides. These can include DNA compacting agents (such as histones), non-infectious vectors (such as plasmids, lipids, liposomes, cationic polymers and cationic lipids) and viral vectors such as viruses and virus-like particles (i.e., synthetic particles made to act like viruses). The vector may further have attached peptide targeting sequences, antisense nucleic acids, and DNA chimeras which include gene sequences encoding for ferry proteins such as membrane translocating sequences ("MTS") and herpes simplex virus-1 ("VP22").

Further therapeutic agents include:

Anti-sense DNA and RNA tRNA or rRNA to replace defective or deficient endogenous molecules Gene delivery agents, which may be either endogenously or exogenously controlled. Examples of endogenous control include promoters that are sensitive to a physiological signal such as hypoxia or glucose elevation. Exogenous control systems involve gene expression controlled by administering a small molecule drug. Examples include tetracycline, doxycycline, ecdysone and its analogs, RU486, chemical dimerizers such as rapamycin and its analogs, etc.

Angiogenic molecules including:
  growth factors: such as acidic and basic fibroblast growth factors, vascular endothelial growth factor, epidermal growth factor, transforming growth factor alpha and beta, platelet-derived endothelial growth factor, platelet-derived growth factor, platelet derived endothelial cell growth factor, tumor necrosis factor α, hepatocyte growth factor, insulin like growth factor, placental growth factor; PR39, angiogenin, prostaglandin E1 and E2, interleukin 8, angiopoietins (I, II. III, IV, etc), androgens, proliferin, granulocyte colony stimulating factor, estrogens
  transcription factors: such as Hif1a, Del1,
  protein kinases: such as Akt Cytotoxic factors or cell cycle inhibitors, including CD inhibitors: such as p53, thymidine kinase ("TK") and other agents useful for interfering with cell proliferation The family of bone morphogenic proteins ("BMP's"): including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Cell survival molecules: including Akt, insulin-like growth factor 1, NF-KB decoys, I-kB, Other therapeutic agents: including Madh6, Smad6, Apo A-1, Small molecule activators or inhibitors of the genes described above including decoys.

Vectors and gene transfer agents including:
  Viral vectors: such as adenoviruses, gutted adenoviruses, adeno-associated virus, retroviruses, alpha virus (Semliki Forest, Sindbis, etc.), lentiviruses, herpes simplex virus, ex vivo modified cells (i.e., stem cells, fibroblasts, myoblasts, satellite cells, pericytes, cardiomyocytes, sketetal myocytes, macrophage, etc.), replication competent viruses (ONYX-015, etc.), and hybrid vectors.
  Nonviral vectors: artificial chromosomes and mini-chromosomes, plasmid DNA vectors (pCOR), cationic polymers (polyethyleneimine, polyethyleneimine (PEI) graft copolymers such as polyether-PEI and polyethylene oxide-PEI, neutral polymers PVP, SP1017 (SUPRATEK), lipids or lipoplexes, nanoparticles and microparticles with and without targeting sequences such as the protein transduction domain (PTD).

A "polynucleotide" is a nucleic acid molecule polymer, such as DNA, RNA and their analogs, having as few as 3 nucleotides, and can include both double- and single-stranded sequences. A "protein" is a polymer of as few as two (dimer) amino acid residues.

Preferably, the pharmaceutically active material is a cell or polynucleotide, more preferably a cell or polynucleotide that is present in the form of a plasmid or that is present in conjunction with virus or virus-like particles. Specific examples of preferred cells include cardiomyocytes, skeletal myoblasts, endothelial cells, and stem cells. Specific examples of preferred virus or virus-like particles include adenovirus, paroviruses such as adeno-associated virus, lentivirus, retrovirus, alpha-virus, papilloma virus, murine leukemia virus, Semliki Forest virus, and so forth.

The pharmaceutically active agents can be provided in essentially any form known in the art, and can be, for example, disposed in a solution, a dispersion, a solid matrix, such as a porous polymer matrix, a biodegradable polymer matrix or a hydrated gel matrix, microparticles and so forth.

According to one embodiment of the invention, at least one component of an incompatible conventional pharmaceutical article is modified by providing it with a surface treatment. All methods of the present invention, including surface treatments, are carried out to prevent a substantial reduction in pharmaceutical efficacy of the pharmaceutically active material.

One form of surface treatment in accordance with the present invention is a chemical passivation treatment. Preferred chemical passivation treatments include those that provide a robust oxide barrier on a metallic surface, such as acid treatment with or without treatment with steam at high temperature. Preferred acids for this purpose include citric acid, nitric acid, and chromic acid. According one preferred embodiment, an incompatible stainless steel component is treated with acid, immediately followed by treatment with steam at high temperature (e.g., by autoclaving). Information concerning chemical passivation of stainless steel can be found, for example, in ASTM Designation: A 967-96 entitled "Standard Specification for Chemical Passivation Treatments for Stainless Steel Parts," the entire disclosure of which is hereby incorporated by reference. Procedures are set forth therein for nitric acid treatment, citric acid treatment, as well as other treatments, including electrochemical treatments.

Other forms of surface treatment include treating the incompatible pharmaceutical article component with solutions or suspensions containing one or more of the following: lipids and liposomes; emulsifying agents and detergents such as glycerin, sodium lauryl sulfate, sodium oleate; proteins, such as albumin, particularly human serum albumin (HSA) and bovine serum albumin (BSA); other natural polymers such as hyaluronic acid, laminin, fibronectin, fibrin, and collagen, as well as glucans and glycosaminoglycans, such as dextrans, dextran sulfate and heparin; synthetic polymers such as polyethylene glycol, polyethylene oxide, polyvinyl pyrrolidone, poloxamers, polyethylenimine, protamine sulfate, polyamidoamine dendrimers, amphiphilic peptides, RGD-oligolysine peptides, and fluorocarbons such as polytetrafluoroethylene (further synthetic polymers are listed below); contrast agents such as iohexol, blood or serum (e.g., from a patient or donor), and so forth. Treatment may be carried out by contacting the agents mentioned above with the incompatible pharmaceutical article component before that component is brought into contact with the therapeutic agent. Treatment may also be carried out by formulating the agents mentioned above directly into the solution or suspension containing the therapeutic agent. For instance, human serum albumin may be formulated into a viral suspension, such as an adenoviral suspension, in order to exert a protective or stabilizing effect. Additionally, the surface treatment may concurrently involve a cleaning process and/or sterilization process to remove surface contaminants or impurities.

In the case of treatment with solutions or suspensions of the above species, these species typically attach to the pharmaceutical article component surface by van der Waals' forces, hydrogen bonding and/or ionic forces. However, a number of schemes are available in the art by which a selected species can be covalently or physically attached to the pharmaceutical article component surface. Examples include attachment via photoactivated hydrogel coatings on polyethylene surfaces. Other examples include covalent immobilization of protein polymers, for example, by contact with silanated surfaces (e.g., glycophase glass) reacted with tresyl chloride, and followed by coupling the $\bar{c}$ amino terminal end of the protein polymer. Still other examples include cross-linked hydrogels/polymer surfaces using water-soluble carbodiimide chemistry.

According to another embodiment of the present invention, at least one incompatible component of a pharmaceutical article is replaced with a more compatible material or provided with a barrier layer of more compatible material. The barrier layers of the present invention are preferably 0.1 micron or greater in thickness, with thicknesses of 50 microns or greater being common.

Polymers are one class of material that can be used to replace the incompatible material or to provide it with a barrier layer.

Polymers appropriate for the practice of the invention include preformed and unformed polymers or hydrogels. Polymers may be crosslinked or uncrosslinked, linear or branched, natural or synthetic, thermoplastic or thermosetting, or biostable, biodegradable, bioabsorbable or dissolvable.

Exemplary polymers include the following polymers and copolymers: polycarboxylic acid polymers and copolymers including polyacrylic acids (e.g., acrylic latex dispersions and various polyacrylic acid products such as HYDROPLUS, available from Boston Scientific Corporation, Natick Mass. and described in U.S. Pat. No. 5,091,205, the disclosure of which is hereby incorporated herein by reference, and HYDROPASS, also available from Boston Scientific Corporation); acetal polymers and copolymers; acrylate and methacrylate polymers and copolymers; cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polybismaleinimides, polyamidimides, polyesterimides, and polyetherimides; polysulfone polymers and copolymers including polyarylsulfones and polyethersulfones; polyamide polymers and copolymers including nylon 6,6, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); anhydride polymers and copolymers including maleic anhydride polymers; polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-butadiene copolymers, acrylonitrile-styrene copolymers, acrylonitrile-butadiene-styrene copolymers, styrene-butadiene-styrene copolymers and styrene-isobutylene-styrene copolymers, polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-,1- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates (e.g., U.S. Pat. No. 5,091,205 describes medical devices coated with one or more polyisocyanates such that the devices become instantly lubricious when exposed to body fluids); polyolefin polymers and copolymers, including polyalkylenes such as polypropylenes, polyethylenes (low and high density, low and high molecular weight), polybutylenes (such as polybut-1-ene and polyisobutylene), poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes (e.g., BAYHYDROL polyurethane dispersions); p-xylylene polymers; polyiminocarbonates; copoly(ether-esters)such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the same.

Preferred polymers include polyethylene (low or high density), polyethylene terephthalate polyester (PET-P), ethylene vinyl acetate polymers, polysulfone, high viscosity acetal homopolymer (such as DELRIN 100), polypropylene, polyether block amides, polyesters, polyether esters, silicone polymers, polyurethanes, styrene-butadiene polymers, polyether imides (such as Poly Penco Ultem 1000), polyurethanes (such as Hydex 301 Isoplast), fluorinated polyalkenes such as polytetrafluoroethylene (PTFE), poly (tetrafluoroethylene-co-hexafluoropropene) (FEP), modified ethylene-tetrafluoroethylene copolymer (ETFE), polyvinylidene fluoride (PVDF), ethylene chlorotrifluoroethylene copolymer (ECTFE)(such as HALAR 500 HF), and so forth. More preferred polymers include polypropylene, polyethylene (low or high density), PET-P, polyether block amides, polyesters, polyether esters, and fluorinated polymers such as PTFE, ETFE, FEP, and PVDF.

Of course, not all of the above polymers will be appropriate for all pharmaceutically active materials. For example, polymers may be incompatible with a given pharmaceutically active material due to the presence of incompatible processing additives or due to the nature of the polymer material itself. Several incompatible combinations of pharmaceutically active and polymer materials are set forth in the Examples below, many of which are believed to be due to the various processing additives used. However, those of ordinary skill in the art will be able to determine which polymers are appropriate for a given pharmaceutically active material with relative ease using, for example, techniques like those used in the Examples.

In general, favorable interactions (e.g., ionic, van der Waals, hydrophobic, etc.) between the material and therapeutic agent should be reduced such as to avoid adsorption of the therapeutic agent onto the surface or inactivation or denaturation by the surface.

Where the polymeric material is of suitable mechanical character, a barrier layer may be provided by simply introducing a preformed member of the polymeric material. As an example, in the case of a lumen made from an incompatible material, a barrier layer can be formed by simply inserting a preformed tube of a more compatible material into the lumen.

In other embodiments, a barrier layer can be formed on an incompatible material surface by means of a number of suitable coating methods, including dipping, spraying, vapor deposition, plasma polymerization and so forth. Preferably, the surface of the incompatible material is provided with a polymer coating by one of the following techniques: (a) forming a solvent dispersion of a polymer of interest, coating a surface of the incompatible material with the dispersion, and removing the solvent, and (b) coating a surface of the incompatible material with a liquid layer of curable polymer resin and curing the resin, for example, with ultraviolet or infrared radiation.

In other embodiments of the present invention, at least one component of a conventional pharmaceutical article is replaced with a more compatible component. Exemplary embodiments include replacement of the incompatible component with a polymeric component formed from a polymer selected from those previously discussed. As always, where the pharmaceutical article contacts the subject, the polymer should be compatible with the subject.

Moreover, the polymer should meet any structural requirements. Numerous methods are available to provide structural integrity or flexibility to polymers. For example, in the event that the pharmaceutical article comprises a needle (or cannula) for delivery or aspiration, a polymeric needle can be fashioned from several of the materials listed above, notably, polyimide, PTFE, PET, polyphenylene sulfide (PPS), polysulfone (PS) and PEEK, which have excellent rigidity and the ability to be sharpened into a needle. Additional materials are disclosed in U.S. Pat. No. 4,838,877, including, polycarbonates, polyetherimides, polymethylpentenes, polyesters, acrylates, polyaramides, polyamides, modified phenylene oxides, and polysulfones. Alternatively, where enhanced strength and/or rigidity are desired, the polymeric material can be reinforced, for example, by fibers. For example, U.S. Pat. No. 5,637,399 discloses a synthetic resin needle of reinforced with combustible fibers whose longitudinal directions are arrayed straight or curvilinearly along the axial length of the needle. Numerous resins are listed, from which one or ordinary skill in that art can select and test for compatibility, for example, using the procedures set forth in the Examples. Metal or ceramic reinforcements may be included in addition to combustible fibers.

In the case of polymer adhesives, an incompatible adhesive may be replaced with a more compatible one. For example, as seen in the Examples below, an adhesive, such as FDA2 or FDA23 (epoxy-based adhesives) can be replaced with a more compatible one, such as HB Fuller 3507 (a urethane-based adhesive). Of course, the incompatible adhesive can also be provided with a barrier layer of a more compatible material.

In other embodiments, an incompatible pharmaceutical article component is replaced or provided with a barrier layer of a more compatible metal. For example, an incompatible pharmaceutical article component may be coated with a barrier layer of gold, titanium or platinum, covered with preformed barrier layers of the same, or replaced by the same.

In still other embodiments, an incompatible pharmaceutical article component is replaced or provided with a barrier layer of a more compatible silica material such as glass or quartz. Glass or quartz materials appropriate for the practice of the invention include fused silica fibers. Such fused silica fibers are flexible and do not take on a set shape after being bent for a given period of time. According to one embodiment, a lumen made of fused silica fibers can be formed. In certain embodiments, such a lumen of fused silica fibers can be inserted into another outer lumen material, such as a metal lumen or a plastic lumen, which outer lumen would provide additional properties such as stiffness, bonding, color, friction resistance (e.g., PTFE), and so forth. In this way, the pharmaceutically active material that travels through the lumen contacts only the fused silica.

Further inorganic barrier layers extending beyond metals and glass that are contemplated include amorphous carbon coatings, other diamond-like coatings, and silicone carbide coatings. A preferred method of forming such inorganic coatings is chemical vapor deposition (CVD) or physical vapor deposition (PVD). The inorganic coating may also be glass or quartz materials such as those above. Surface modifications such as sintering are also possible.

Below are examples that are offered for illustrative purposes only, and are not intended to limit the scope of the present invention in any way.

EXAMPLES

Example 1

Time Course Evaluation of Virus Compatibility

A CMV-β-gal adenovirus (i.e., an adenoviral vector driven by a CMV (cytomegalovirus) promoter and encoding a β-galactosidase (β-gal) reporter gene) was used as a stock virus in this example.

Stock virus having a viral titer of $3 \times 10^7$ (also referred to herein as $3 \times 10^7$ or 3E+07) infectious units/ml (IU/ml) (also referred to herein as pfu/ml) was incubated in catheters at 37° C. The catheters used were endocardial catheters like those described in international patent application WO/9922655, the disclosure of which is hereby incorporated by reference in its entirety. These catheters have a proximal portion formed from heat-treated stainless steel and a distal portion formed from a nitinol hypotube (referred to in these examples as "catheter" or "injection catheter" or "needle injection catheter"); the hub is comprised of polycarbonate. After the allotted amount of time (0–30 minutes, where 0 minutes refers to the situation in which the viral solution was flushed through the catheter), the viral solution was pushed through the catheter into a polypropylene eppendorf tube. The viral solution was then titered on HeLa cells (human epidermoid carcinoma cells). For this purpose, HeLa cells were first plated out in well plates at 70% confluency the day before the experiment. Prior to contacting the HeLa cells, the viral solution was diluted appropriately in infection media (DMEM (Dulbecco's Modified Eagle's Medium)+2% FBS(Fetal Bovine Serum)) to achieve a result of 1E+02–1E+03 infected cells per well. The diluted virus was added to the HeLa cells in the wells and incubated at 37° C. for 1 hour. 5 mls of DMEM+10% FBS were then added to each well, followed by incubation for 24–30 hours at 37° C. After aspirating of the media, the cells were fixed in 0.5% glutaraldehyde in PBS (phosphate buffered saline) for 10 minutes. The cells were washed twice in PBS and stained using an X-gal staining solution overnight at 37° C. (X-gal is 5-bromo-4-chloro-3-indolyl-β-D-galactoside, which is hydrolyzed by β-galactosidase to form a blue product). Blue cells were counted the next day to determine the titer.

Data are presented in the table to follow for 0 (simple flush through), 5, 10 and 30 minutes in the catheter. The data are presented in the table in terms of cell counts (accounting appropriately for dilution), in terms of absolute titer (IU/ml), and in terms of percentage of the titer of stock virus (3.0E+07 IU/ml).

FIG. 1 presents these data in terms of absolute virus titer (log scale) and FIG. 2 presents these data relative to the viral stock titer (linear scale). These data suggest that residency in the catheter results in a deterioration of viral efficacy and that this incompatibility effect increases with increasing exposure time.

| Time (min.) | Pos. Cells #1 | Pos. Cells #2 | Pos. Cells #3 | Titer (IU/ml) | Std. Dev. | % of stock |
|---|---|---|---|---|---|---|
| 0 | 7400000 | 10800000 | 5900000 | 8.03E+06 | 2.51E+06 | 26.78 |
| 5 | 3400000 | 4100000 |  | 3.75E+06 | 4.95E+05 | 12.50 |
| 10 | 3900000 | 2400000 | 1800000 | 2.70E+06 | 1.08E+06 | 9.00 |
| 30 | 300000 | 300000 | 300000 | 3.00E+05 | 0.00E+00 | 1.00 |

Example 2
Time Course Evaluation of Virus Compatibility

Procedures similar to Example 1 were followed, except that an additional initial viral titer (4E+08 IU/ml) was examined, both in a catheter and as a control. For the control, the virus was exposed to a polypropylene vial for the appropriate period.

The number of positive cells was counted: (1) after 0 (flush through) and 30 minutes in the control vial (4E+08 IU/ml), (2) after 0 (flush through) and 30 minutes in the catheter, using the same stock virus titer as the control (4E+08 IU/ml), and (3) after 0 (flush through) and 30 minutes in the catheter, using a lower stock virus titer (3E+07 IU/ml).

Data are presented in FIG. 3, which presents these data as a percentage of viral stock titer. As in Example 1, there is a significant drop in virus activity as a function of incubation time. For a virus stock titer of 3E+07 IU/ml, a flush through resulted in a 75% loss of activity relative to the viral stock while a 30-minute incubation resulted in a 99% loss of activity. At the higher titer of virus, 4E+08 IU/ml, a flush through the catheter resulted in only a 6% loss of activity. However, 97% activity was lost after 30 minutes, consistent with the results at the lower titer. Hence, simply increasing viral titer may not appear to be an effective solution to the loss in viral efficacy observed.

Example 3
Time Course Evaluation

Procedures similar to Examples 1 and 2 were followed for viral solutions having titers of 3.0E+7 IU/ml and 4.5E+8 IU/ml. Positive cells were counted after 0 (flush through), 5, 10 and 30 minutes in the catheter. Data are presented in FIG. 4, which shows a more pronounced drop in activity for the lower concentration over shorter incubation times. This difference, however, becomes less significant at longer incubation times, as also seen in Example 2.

Example 4
Material Compatibility

In this example, the procedures of Example 1 were followed, except viral titers were measured after exposure to various materials for 30 minutes. In some examples, a stock viral titer of 5E+08 was used. In others (namely, the second control, the injection catheter, and the passivated injection catheter), a stock viral titer of 4E+08 was used. For a control, the stock virus was placed in a polypropylene vial for 30 minutes.

The lumen materials for this example have a proximal portion approximately 48" in length and a distal portion measuring approximately 14" in length. The overall length is slightly less than 62", because the distal end is inserted into the proximal end. (Note that Groups #3 and #4 below were single pieces of 5 ft. lengths.)

Lumen materials for this example were as follows (dimensions are in inches if not otherwise indicated): (1) injection catheter with a proximal end (0.013"×0.025") formed from heat-treated stainless steel, a distal end (0.009"×0.014") formed from a nitinol hypotube, and containing polycarbonate hub (See Example 1 above); (2) 0.013×0.025 stainless steel hypotube (proximal end) swaged to a 0.007×0.014 stainless steel hypotube (distal end); (3) 0.0093×0.014 nitinol hypotube; (4) 0.010×0.018 stainless steel hypotube; (5) 0.013×0.025 stainless steel hypotube (proximal end) and 0.0093×0.014 nitinol hypotube (distal end); the nitinol was insulated the with a small piece of 0.013×0.024 Cristamid MS1100 (semiaromatic polyamide; Elf Atochem), the larger stainless steel hypotube collar was bonded over the joint; the proximal stainless steel hypotube was not allowed to touch the distal length of nitinol; (6) full length HDPE necked to 0.010×0.015 on the distal end and 0.013×0.025 on the proximal end; (7) injection catheter of group #1, with passivation treatment.

The passivation process was conducted as set forth in ASTM standard A967-96 "Chemical passivation of stainless steel parts". Specifically, the catheter was treated with a 7% weight to volume citric acid solution in water for 7 minutes at 70° C. Immediately after removal from the citric acid solution, the catheter was thoroughly rinsed in water multiple times.

Absolute titers are presented in FIG. 5 (log scale), and titer as a percentage of viral stock are presented in FIG. 6 (linear scale). These data suggest that all of the lumen materials tested had a negative effect on viral efficacy.

In particular, all untreated lumens containing stainless steel (stainless steel per se, stainless steel swaged to nitinol, stainless steel swaged to nitinol with insulated joint and injection catheter) reduced virus activity to only 1–2% of the stock virus titer. Similarly, virus incubated in nitinol retained only 6% of its original activity. Virus incubated within the passivated injection catheter retained 15% of its original activity. 50% of the virus activity was lost post incubation in the polyethylene lumen.

These data suggest that certain metals, such as stainless steel and nitinol, result in substantial loss of viral efficacy as compared to certain polymers, such as polypropylene (control) and polyethylene. The presence of flow in the polymeric and metal lumens versus the lack of flow in the control sample may have negatively impacted virus activity in addition to a detrimental effect as a result of the high surface area to volume ratio with the lumen samples.

Moreover, these data suggest that metal can be passivated by proper chemical treatment. Without wishing to be held to any particular theory, it is believed that the citric acid solution acts to remove free iron and iron oxides and to build up a surface layer comprised primarily of chromium oxides. The resulting surface is non-electrochemically active and is believed to be relatively inert to other chemical and physico-chemical interactions.

It is known that joints between dissimilar metals can create a galvanic reaction in the presence of an electrolyte, resulting in the release of free metal ions and that this may be prevented by insulating the joint between the two metals. Hence, these data also suggest that the loss in efficacy seen with lumens having stainless steel/nitinol joints is not due to a galvanic interaction between nitinol and stainless steel, since the data for insulated and uninsulated joints did not statistically differ.

Example 5

Material Compatibility with Adenovirus

In this Example, viral solution, titer=$4.8\times10^8$ IU/ml, was incubated with a ⅜ inch diameter×1 inch long cylindrical material sample for 30 minutes at 37° C. in polypropylene tubes. The control was virus placed in a polypropylene tube without a material sample. The activity of the virus was assessed after the 30-minute incubation period. The results are shown in FIG. 7 and also include a 30-minute incubation within a REMEDY infusion balloon catheter.

Polymeric materials found to be less compatible with virus include LEXAN polycarbonate (available from General Electric), polyimide (VESPEL SP-1; DuPont), poly ether ether ketone (PEEK) (KETRON; DSM Engineering Plastic Products), nylon 6/12 (Poly Penco), and acrylonitrile/butadiene/styrene resin. Polymeric materials that appear to be more virus-compatible include polypropylene, high-density polyethylene (HDPE), virgin polytetrafluoroethylene (PTFE), modified ethylene-tetrafluoroethylene copolymer (ETFE) (TEFZEL; DuPont) and poly (tetrafluoroethylene-co-hexafluoropropene)(FEP) (FEP 100; DuPont). Polyethylene terephthalate polyester (PET-P) (ERTALYTE; DSM Engineering Plastic Products) was also more compatible.

Consistent with FIGS. 5 and 6, virus activity dropped significantly in the presence of stainless steel (type 304). The nitinol tested in FIGS. 5 and 6 (available from Raychem Corp. and composed of 55.8% nickel with a balance of titanium) was tested as a catheter including a polycarbonate manifold. Since polycarbonate has been found to be less compatible with virus, the compatibility of Nitinol was uncertain from FIGS. 5 and 6. FIG. 7 indicates that Nitinol is more compatible than stainless steel at 20% activity retained after a 30-minute incubation. However, it is less compatible (statistically significant) than the more compatible polymers apart from PTFE. Among adhesives, HB Fuller 3507 (a urethane-based adhesive available from HB Fuller) was found to be more compatible with virus than FDA2 or FDA23 (epoxy-based adhesives available from Tracon).

Virus incubated within the REMEDY catheter, an infusion balloon catheter available from Boston Scientific Corporation, Natick, Mass., retained only 5% virus activity, consistent with the fact that this catheter contains a polyimide shaft material.

Example 6

Syringe Compatibility with Adenovirus

Virus solution, initial titer=$4.5\times10^8$ IU/ml, was incubated within a needle injection catheter like that of Example 1, within a 1 ml polypropylene syringe with a 27 g needle attached (similar to those commonly used in epicardial injections) and within a 100 μl glass syringe without an attached needle. The control is a polypropylene tube. The results are shown in FIG. 8. This experiment indicates that the glass syringe is comparable to polypropylene, with about 40% virus activity remaining after a 30-minute incubation. Also, virus injection from conventional needle/polypropylene syringe assemblies also result in a reduction of virus activity, potentially due in part to the stainless steel needle.

Example 7

Effect of BSA and PBS Flush on Viral Efficacy

Viral solution (initial titer $5.5\times10^8$) was incubated in a control vial, an untreated needle injection catheter (like that of Example 1), a needle injection catheter treated with BSA (bovine serum albumin) and a needle injection catheter treated with phosphate-buffered saline (PBS). The BSA-treated catheter was provided by flushing a catheter with a 1% aqueous solution of BSA prior to incubation with virus. The PBS treated catheter was similarly flushed with PBS. The stock virus titer for this example was 5.5E+08 IU/ml and the incubation time was 30 minutes.

Data are presented in FIG. 9 as a percentage of virus stock titer (linear scale). Virus incubated in the BSA-treated catheter retained 76% of its efficacy, compared to sharp drop in efficacy for the untreated and PBS-treated catheters.

These data suggest that a reduction in viral efficacy in the catheter can be substantially diminished by treatment with BSA. Without wishing to be held to any theory, the albumin may provide a barrier between the metal and virus. Alternatively, dissolved albumin may have a stabilizing effect on the virus in suspension. Therefore, the addition of albumin directly to the virus formulation would be expected to exert a similar effect. The resulting effect would be dependent on the concentration of albumin added to the formulation. These effects are explored in Example 9 below.

Example 8

Effect of HSA and PBS on Virus Activity

A 5% solution of HSA (human serum albumin) (U.S.P. Albutein 5% Solution, made by Alpha Therapeutic Corporation in Los Angeles, Calif.) was pre-flushed through a needle injection catheter like that of Example 1 prior to virus incubation. Initial viral titer was $5\times10^8$ IU/ml. The catheters were filled, and 50 μl of virus was pushed out of each catheter and assayed after 5 minutes. Additional 50 μl volumes were pushed out every 5 minutes. Since the dead space in the catheter is ~150–160 μl and since the catheter design does not promote back-mixing, one would expect a decrease in virus activity over the first 15 minutes ($1^{st}$ injection resided in the catheter for 5 minutes, $2^{nd}$ injection resided 10 minutes and $3^{rd}$ resided 15 minutes) and a leveling off between 15 and 25 minutes ($3^{rd}$ through $5^{th}$ injections resided in the catheter for a total of approximately 15 minutes). FIG. 10 indicates that a PBS pre-flush does not exert a protective effect on the virus, consistent with the results of the previous example. Additionally, the expected trend as a function of time is indeed observed for the PBS. The HSA pre-flush, however, does preserve virus activity relative to the PBS pre-flush. The protective effect of HSA is sustained through all 5 injections.

Example 9
Effect of HSA Added to Adenovirus Suspension

A 5% solution of HSA (human serum albumin) (U.S.P. Albutein 5% Solution, made by Alpha Therapeutic Corporation in Los Angeles, Calif.) was added to an adenoviral suspension containing $5\times10^8$ IU/ml virus to achieve total HSA concentrations of 0% (no addition), 0.005% and 0.1%, and these suspensions were incubated within a needle injection catheter like that of Example 1 for 30 minutes. The solution was removed and the activity of the adenovirus was assayed. The results are presented in FIG. 11, which demonstrates that the addition of HSA directly to the virus suspension has a concentration-dependent protective effect on adenovirus activity. Adenovirus in a solution of 0.1% HSA has a significantly greater activity (82%) post incubation within the catheter relative to adenovirus without added HSA (1.6%).

Example 10
Viral Adsorption Study

In this example, OD 260 (optical density at a wavelength of 260 nm) data were taken for stock virus, stock virus after 1:10 dilution in PBS, stock virus after flushing it though an injection catheter, stock virus after incubation in an injection catheter for 30 minutes, and stock virus after incubation in polyethylene (high density) for 30 minutes. Stock virus titer in this example was 1E+09 IU/ml.

OD 260 provides data related to viral concentration, which data is independent of its biological activity. OD 260 data for the virus stock (1E+09 IU/ml) without exposure to the catheter (control), after flushing through the catheter, and after an incubation time of 30 minutes in the catheter are presented in FIG. 12. These data suggest that the concentration of viral particles is effectively the same for samples unexposed to the injection catheter, exposed to the injection catheter during the brief flush-through procedure and exposed to the injection catheter for 30 minutes. These data, in combination with data from the examples above, suggest that the catheter does not retain appreciable amounts of virus, in some fashion (e.g., by adsorption), but rather acts predominantly to inactivate the virus. (FIG. 13 includes an absorbance value for a 1:10 dilution of the stock virus, indicating the sensitivity of the method.)

Figure 13:
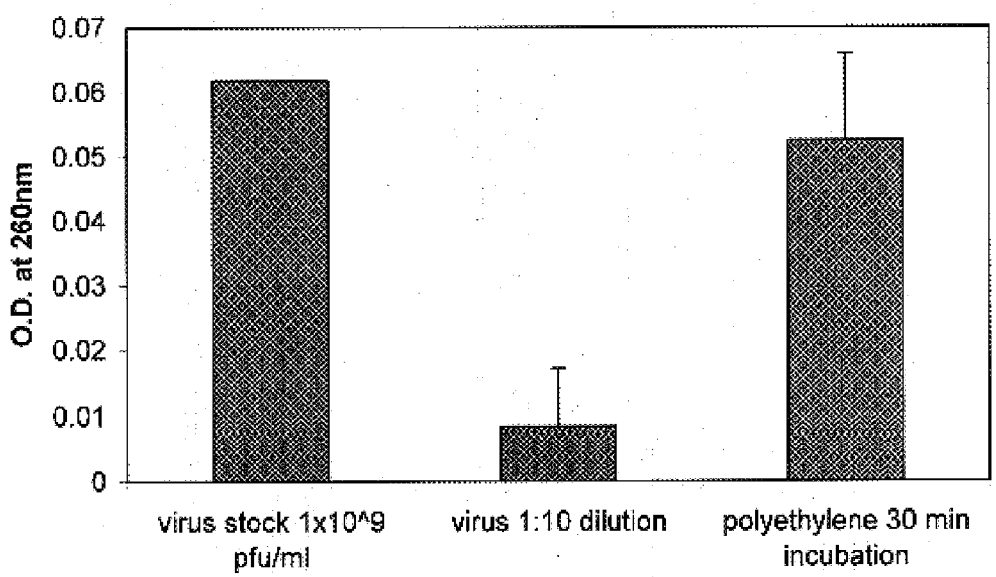
FIG. 13 presents OD 260 data for (a) virus stock (b) virus stock after 1:10 dilution, and (c) virus stock after 30 minutes incubation in a polyethylene lumen.

OD 260 data for virus stock (1E+09 IU/ml), for the virus stock at 1:10 dilution (1E+08 IU/ml), and for the virus stock after incubation in polyethylene for 30 minutes are presented in FIG. 13. As expected, the OD 260 after a 1:10 dilution of the virus stock is on the order of one-tenth that of the undiluted virus stock, according to Beer's Law. Moreover, the differences between the OD 260 of the virus stock and the virus stock after 30 minutes in polyethylene, while different, do not appear to be statistically different. These data, in combination with data from the examples above, suggest that polyethylene may retain virus (e.g., by adsorption), but predominantly acts to inactivate the virus.

Example 11
Viral and Non-viral Vector Activity

Viral and non-viral gene vector solutions were incubated (a) in a polypropylene control vial, (b) in an untreated needle injection catheter like that of Example 1, and (c) in a needle injection catheter like that of Example 1, which has been lined with Pebax® 5533, a polyether block amide. Pebax® polymers are available from Elf-Atochem.

Three gene vector solutions were investigated. The first gene vector solution was an adenoviral vector like that used in Example 1. The second gene vector solution was an adeno-associated viral vector (AAVCMVLacZ) having a titer of $7\times10^8$ IU/ml. The third gene vector solution contained 10 µg/ml plasmid vector (a 3958 bp plasmid with the LacZ gene and a CMV promoter/enhancer).

B-galactosidase assays HeLa cells were injected at 70% confluency with either catheter of agent (AdCMV-LacZ, AAVCMV-LacZ, or Plasmid DNA pNGVL-LacZ) in infection media (DMEM+2% FBS) for 1 h at 37 C. Growth medium (DMEM+2% FBS) was added, and the cells were incubated for an additional 24–30 hr at 37° C. Cells were lysed and incubated with O-nitrophenyl beta-D-galactoside to quantify the beta-galactosidase.

Sample titers were interpolated from a calibration curve and agent activity was expressed relative to the polypropylene control groups. Data are presented in FIG. 14a as a percentage of vector stock titer (linear scale). The untreated catheter is designated G1-Stiletto in FIG. 14a, while the Pebax®-treated catheter is designated G2-Stiletto. Both viral gene vectors incubated in the Pebax®-lined catheter resulted in significantly greater activity relative to the catheter without the Pebax® lining. While comparison of plasmid DNA did not reveal significant differences in transfection efficiency between the catheters, there is evidence of structural damage to the plasmid DNA upon incubation in the unlined catheter, which is observed as an increase in the amount of nicked DNA, which runs at a higher apparent molecular weight. Specifically, FIG. 14b is an assessment of plasmid DNA structural integrity using gel electrophoresis. Lanes C1–C2: polypropylene control samples; lanes 1–5: unlined catheter; lanes 6–10 Pebax lined catheter. Each lane represents effluent from a single catheter (n=5 per catheter group). The unlined catheter samples show ingrowth of an apparently higher molecular weight band, which is indicative of structural damage to the DNA (i.e. nicking of the circular DNA).

These data indicate that a reduction in vector efficacy in the catheter is observed for a broad range of vector types and that this reduction can be substantially diminished by providing an appropriate lining within the catheter.

Example 12
Cell Viability

Cardiomyogenic cells (CMG) were plated at approximately 200,000 per 10 cm plate, cultured in Iscove's modified Dulbecco's medium (DMEM) (Gibco BRL Cat. #12440-053) supplemented with 20% heat-inactivated fetal calf serum (Summit Biotechnology, Fort Collins Colo., Cat. #FP-100-05, lot FA1015), penicillin-streptomycin (100 U/mL 100 mg/mL) (Gibco BRL Cat. #14040-133), glutamine (2 mM) (Gibco BRL Cat. # 25030-081), and maintained at 5% $CO_2$, 33° C. Prior to harvesting cells for experimentation, cells were briefly treated with trypsin, and the trypsin was inactivated in excess growth medium. Cells were collected by centrifugation, counted, and resuspended in Dulbecco's phosphate-buffered saline (DPBS) with $Mg^{2+}/Ca^{2+}$ (Gibco BRL, Cat. #14040-133) at the concentration indicated in the text. This cell-containing PBS solution was kept on ice. The cell suspension was loaded into the catheters, incubated for 30 minutes at 37° C., recovered from the catheters using an air-filled syringe, and counted. Cell viability was determined by Trypan Blue dye exclusion. The number of viable cells recovered from the catheters was normalized to that obtained from controls consisting of cells subjected to a 30 minute incubation at 37° C. following loading into Eppendorf microcentrifuge tubes. All results are expressed as a mean+/– SEM, and comparisons were analyzed using ANOVA and Student's T-test. P<0.05 was considered statistically significant. All statistical data were analyzed using Microsoft Excel (Redmond, Wash.).

Data are presented in FIG. 15 as a percentage of viable cell recovery (linear scale). In all cases, cells incubated in the Pebax®-lined catheter (designated G2-Stiletto in FIG. 15) retained greater activity relative to the catheter without the Pebax® lining (designated G1-Stiletto in FIG. 15). This effect is more pronounced at lower cell concentrations ($5\times10^5$ cells/ml) than it is at higher cell concentrations ($5\times10^6$ cells/ml).

These data indicate that, in addition to adversely affecting gene vector efficacy as discussed above, the catheter also adversely affects the efficacy of whole cells. As with the previous data, these data further indicate that the adverse effects of the catheter can be substantially diminished by providing an appropriate lining within the same.

Example 13
Buffer Effects

Four viral solutions, each with an initial titer of $1\times10^9$ IU/ml, were incubated for 30 minutes within (a) a needle injection catheter like that of Example 1 and (b) a needle injection catheter like that of Example 1 that has been lined with Pebax® 5533. The following buffer solutions were used for the viral solutions: (1) a solution of 0.1% glycerol in PBS, (2) a solution of 10% glycerol in 10 mM tris (hydroxymethyl)aminomethane buffer, (3) a solution of 4% sucrose in PBS and (4) a solution of 4% sucrose in 10 mM tris(hydroxymethyl)aminomethane buffer. The control was a polypropylene tube.

Data are presented in FIG. 16 as a percentage of virus stock titer (linear scale). This experiment indicates that a reduction in gene vector efficacy in the catheter extends over a broad range of buffer systems and, as above, that this reduction can be substantially diminished by providing the catheter with an appropriate lining.

Example 14
Polyether Block Imide and Silicone as Barrier Layers

A viral solution with an initial titer of $1\times10^9$ IU/ml was exposed to various substrates for 30 minutes. The substrates were as follows: (1) a stainless steel hypotube (0.013 inch ID×0.025 inch OD×30 cm length) coated with a mixture of Dow Coming MDX4, an amino-functional silicone, and 360 Medical Fluid, a linear silicone that serves as a plasticizer; (2) a stainless steel hypotube (0.013 inch ID×0.025 inch OD×30 cm length) coated with one application of a 5% MDX4 solution only; (3) a stainless steel hypotube (0.013 inch ID×0.025 inch OD×30 cm length) coated with methyltriacetoxysilane, a low molecular weight silane; (4) a stainless steel hypotube (0.013 inch ID×0.025 inch OD×30 cm length) coated with Pebax® 5533; (5) a 0.013 inch× 0.025 inch×ca. 30 cm stainless steel hypotube; (6) a 0.0093 inch×0.014 inch×30 cm nitinol hypotube and (7) a nitinol hypotube (0.0093 inch×0.014 inch×ca. 30 cm) coated with Pebax(® 5533. The control is a polypropylene tube. After incubation, vector activity was assessed using the techniques of Example 11.

Data are presented in FIG. 17 as a percentage of virus stock titer (linear scale). This experiment, along with FIG. 6, which contains data for the uncoated stainless steel and nitinol lumens, demonstrates that there is a reduction in vector efficacy for both stainless steel and nitinol, and that this reduction can be substantially diminished by providing an appropriate coating.

Example 15
Effect of Catheter Shaft Construction on Viral Efficacy

A viral solution with an initial titer of $1\times10^9$ IU/ml was exposed to various catheter constructions for 30 minutes. The predominant material in these catheter constructions is the shaft material. Shaft materials are as follows: (1) stainless steel, (2) polyether block amide (Pebax® 5533 available from Elf Atochem), (3) polyethylene (Chevron 9640 from Chevron Phillips), (4) polyimide, (5) polyether block amide (Pebax® 7033 available from Elf Atochem), and (6) polyethylene. The control is a polypropylene tube. After incubation, vector activity was assessed using the techniques of Example 1.

Data are presented in FIG. 18 as a percentage of virus stock titer (linear scale). Dramatic reductions in vector efficacy are seen for catheters with stainless steel and polyimide shafts. On the other hand, with catheters having polyether block amide shafts and polyethylene shafts, the reductions observed are less dramatic, if present at all. These data are consistent with the data found, for example, in FIG. 7.

Example 16
Material Compatibility with Adenovirus

In this Example, an adenoviral viral solution with an initial titer of $1\times10^9$ IU/ml was incubated with lumen sample material for 30 minutes at 37° C. Lumen materials are as follows: (1) a stainless steel hypotube (0.013 ID×0.025 OD×30 cm length), (2) Pebax® 2533, a polyether block amide, tubes (0.0192" ID×0.0352" OD, ca 20" length available from Elf Atochem, (3) tubes (0.0192" ID×0.0352" OD, ca 20" length) of Pebax® 5533, a polyether block amide available from Elf Atochem, (4) tubes (0.0192" ID×0.0352" OD, 20" length) of Pebax® 7033, a polyether block amide available from Elf Atochem, (5) tubes (0.024" ID×0.027" OD, 21.5" length) of Amitel EM550, a polyether ester available from DSM, (6) tubes (0.022"×0.046", 12.5" length) of Amitel EM740, a polyether ester available from DSM, (7) tubes (0.027 inch ID×0.037 inch OD, 12.5" length) of Hytrel 7246, a polyester available from Dupont, (8) tubes (0.025 inch ID×0.034 inch OD, 12.5" length) of Cristamid MS1100, an amorphous nylon polymer available from Elf Atochem, and (9) tubes (0.025 inch ID×0.034 inch OD, 12.5" length) of Rilsan Aesno Nylon 12 available from Elf Atochem. After incubation, vector activity was assessed using the techniques of Example 11.

Data are presented in FIG. 19 as a percentage of virus stock titer (linear scale). In general, polymeric materials show a significant improvement in virus compatibility as compared to stainless steel. However, amongst the polymeric materials the polyether amides (Pebax® family) and polyether/esters preserve virus activity significantly better than the nylon (Cristamid).

Example 17
Effect of Fluoropolymer on Adenovirus Compatibility

In this Example, an adenoviral solution with an initial titer of $1.0\times10^9$ IU/ml, was incubated for 30 minutes at 37° C. in association with the following: (1) needle injection catheter, like that of Example 1, (2) a PTFE plug (⅜ inch diameter×1 inch long cylinder), (3) an FEP plug (⅜ inch diameter×1 inch long cylinder) (4) a 0.013 inch ID×0.025 inch OD×30 cm length tube coated with Xylan-8110, a PTFE polymer available from Whitford Co in a coating formulation available from Thermech, (5) a 0.013 inch ID×0.025 inch OD×30 cm length tube coated with Xylan-1220, a FEP polymer available from Whitford Co., which is formulated in a coating available from Thermech, (6) a 0.013 inch ID×0.025 inch OD×30 cm length tube constructed from FEP available from Endura, (7) a stainless steel tube lined with PTFE liner (ca 0.01" ID), (8) a lumen of PTFE having an internal diameter of 0.012 inch, (9) a lumen of PTFE having an internal diameter of 0.015 inch. The control is a polypropylene tube. After incubation, vector activity was assessed using the techniques of Example 1.

Data are presented in FIG. 20 as a percentage of virus stock titer (linear scale).

The virus compatibility experiments revealed no significant difference between these teflon-coated surfaces and the bare needle injection catheter. Elemental analysis (ICP and X-ray diffraction) of the lumens detected a spectrum of metal species (Cr, Fe, Mn, Ni, and Ti) on all coated surfaces. Although the ICP results varied within a treatment group (also observed for the uncoated lumen group), these results indicate that the inner lumens are heterogeneous surfaces. Most importantly, and corroborated by the SEM-X-ray analysis, the teflon-covered were not adequately coated. Recognizing the inherent difficulty in coating the narrow, 0.009" inner lumen, a teflon-lined polyimide lumen was extruded and tested. Nonetheless, loss of virus activity was still observed. It is known, however, that the processing of fluorinated polymers into catheter shafts requires the addition of additives. These materials, which include xylene, glycerine and octylphenoxypolyethoxyethanol, may have a significant effect on virus compatibility, highlighting the importance of testing the complete article components for biological activity.

The present invention provides methods and pharmaceutical articles that overcome incompatibility problems of the prior art. Although the present invention has been described with respect to several exemplary embodiments, there are many other variations of the above-described embodiments that will be apparent to those skilled in the art, even where elements have not explicitly been designated as exemplary. It is understood that these modifications are within the teaching of the present invention, which is to be limited only by the claims appended hereto.

We claim:

1. A pharmaceutical article for contact with a pharmaceutically active material comprising:

an endoluminal catheter comprising a drug delivery lumen through which the pharmaceutically active material passes, said lumen comprising an incompatible material selected from stainless steel and titanium alloy that acts to substantially reduce pharmaceutical effectiveness of said pharmaceutically active material upon contacting said incompatible material; and a barrier layer comprising a polymeric material disposed between said incompatible material and said pharmaceutically active material, said barrier layer being more compatible with said pharmaceutically active material than is said incompatible material, and said barrier layer acting to diminish said substantial reduction in the pharmaceutical effectiveness of the pharmaceutically active material.

2. The pharmaceutical article of claim 1, wherein said titanium alloy is a nickel-titanium alloy.

3. The pharmaceutical article of claim 1, wherein said polymeric material comprises a material selected from polyalkylene polymers and copolymers, fluorocarbon polymers and copolymers, polyester polymers and copolymers, polyether polymers and copolymers, silicone polymers and copolymers, and polyurethane polymers and copolymers.

4. The pharmaceutical article of claim 1, wherein said polymeric material comprises a material selected from polyethylenes, polypropylenes, polytetrafluoroethylenes, poly(tetrafluoroethylene-co-hexafluoropropenes), modified ethylene-tetrafluoroethylene copolymers, ethylene chlorotrifluoroethylene copolymers, polyvinylidene fluorides, polyethylene oxides, polyethylene terephthalates, silicones, polyurethanes, polyether block amides, and polyether esters.

5. The pharmaceutical article of claim 1, wherein said barrier layer is a polymer coating.

6. The pharmaceutical article of claim 1, wherein said barrier layer is a preformed polymer layer.

7. The pharmaceutical article of claim 1, further comprising said pharmaceutically active material, wherein said pharmaceutically active material comprises a polynucleotide.

8. The pharmaceutical article of claim 1, further comprising said pharmaceutically active material, wherein said pharmaceutically active material is selected from viral vectors, plasmids and whole cells.

9. The pharmaceutical article of claim 1, wherein said catheter is a perfusion catheter.

10. The pharmaceutical article of claim 9, wherein said polymeric material comprises a material selected from polyalkylene polymers and copolymers, fluorocarbon polymers and copolymers, polyester polymers and copolymers, polyether polymers and copolymers, silicone polymers and copolymers, and polyurethane polymers and copolymers.

11. The pharmaceutical article of claim 9, wherein said polymeric material comprises a material selected from polyethylenes, polypropylenes, polytetrafluoroethylenes, poly(tetrafluoroethylene-co-hexafluoropropenes), modified ethylene-tetrafluoroethylene copolymers, ethylene chlorotrifluoroethylene copolymers, polyvinylidene fluorides, polyethylene oxides, polyethylene terephthalates, silicones, polyurethanes, polyether block amides, and polyether esters.

12. The pharmaceutical article of claim 9, further comprising said pharmaceutically active material, wherein said pharmaceutically active material comprises a polynucleotide.

13. The pharmaceutical article of claim 9, further comprising said pharmaceutically active material, wherein said pharmaceutically active material is selected from viral vectors, plasmids and whole cells.

14. A needle injection catheter for delivery of a pharmaceutically active material into bodily tissue, said needle injection catheter comprising:

a metallic drug delivery lumen through which the pharmaceutically active material passes, said drug delivery lumen comprising an incompatible material which acts to substantially reduce pharmaceutical effectiveness of said pharmaceutically active material upon contact with said incompatible material; and a barrier layer comprising a polymeric material disposed between said incompatible material and said pharmaceutically active material, said barrier layer being more compatible wit said pharmaceutically active material than is said incompatible material, and said barrier layer acting to diminish said substantial reduction in the pharmaceutical effectiveness of the pharmaceutically active material.

15. The needle injection catheter of claim 14, wherein said needle injection catheter comprises: (a) a body portion, said body portion further comprising a metallic lumen, (b) a barrier layer lining said lumen, and (c) a needle portion in fluid communication with said body portion.

16. The needle injection catheter of claim 14, wherein said polymeric material comprises a material selected from polyalkylene polymers and copolymers, fluorocarbon polymers and copolymers, polyester polymers and copolymers, polyether polymers and copolymers, silicone polymers and copolymers, and polyurethane polymers and copolymers.

17. The needle injection catheter of claim 14, wherein said polymeric material comprises a material selected from polyethylenes, polypropylenes, polytetrafluoroethylenes, poly(tetrafluoroethylene-co-hexafluoropropenes), modified ethylene-tetrafluoroethylene copolymers, ethylene chlorotrifluoroethylene copolymers, polyvinylidene fluorides, polyethylene oxides, polyethylene terephthalates, silicones, polyurethanes, polyether block amides, and polyether esters.

18. The needle injection catheter of claim 14, further comprising said pharmaceutically active material, wherein said pharmaceutically active material comprises a polynucleotide.

19. The needle injection catheter of claim 14, further comprising said pharmaceutically active material, wherein said pharmaceutically active material is selected from viral vectors, plasmids and whole cells.

* * * * *

UNITED STATES PATENT AND TRADEMARK OFFICE
CERTIFICATE OF CORRECTION

PATENT NO.    : 6,800,073 B2
DATED         : October 5, 2004
INVENTOR(S)   : Maria Palasis et al.

It is certified that error appears in the above-identified patent and that said Letters Patent is hereby corrected as shown below:

<u>Title page,</u>
Item [75], Inventors, insert the following:
-- Maria Palasis, Wellsley, MA (US)
  Wendy Naimark, Cambridge, MA (US)
  Timothy Mickley, Elk River, MN (US)
  Louis Ellis, St. Anthony, MN (US) --

<u>Column 2,</u>
Line 38, before "injection" change "need" to -- needle --.

<u>Column 8,</u>
Line 50, after "According", insert -- to --.

<u>Column 11,</u>
Line 60, after "needle, delete "of".

<u>Column 12,</u>
Line 49, before "or 3E+07," change "3X10$^7$" to -- 3X10$^{\wedge 7}$ --.

<u>Column 14,</u>
Line 42, after "insulated", delete "the".

<u>Column 15,</u>
Line 30, after "control", change "was virus" to -- virus was --.

<u>Column 16,</u>
Line 32, before "sharp", insert -- a --.

<u>Column 17,</u>
Line 21, after "flushing it", change "though" to -- through --.

<u>Column 18,</u>
Line 6, after "24-30", change "hr" to -- hrs --.
Line 25, change "Pebax" to -- Pebax® --.

<u>Column 21,</u>
Line 3, after "teflon-covered", insert -- surfaces --.

UNITED STATES PATENT AND TRADEMARK OFFICE
CERTIFICATE OF CORRECTION

PATENT NO. : 6,800,073 B2
DATED : October 5, 2004
INVENTOR(S) : Maria Palasis et al.

It is certified that error appears in the above-identified patent and that said Letters Patent is hereby corrected as shown below:

Column 22,
Line 36, after "compatible", change "wit" to -- with --.

Signed and Sealed this

Twelfth Day of April, 2005

JON W. DUDAS
*Director of the United States Patent and Trademark Office*